(12) United States Patent
Pelletier et al.

(10) Patent No.: US 6,323,008 B1
(45) Date of Patent: *Nov. 27, 2001

(54) METHODS FOR PRODUCING SIALYLOLIGOSACCHARIDES IN A DAIRY SOURCE

(75) Inventors: Marc Pelletier, Doylestown; William A. Barker, West Chester; David J. Hakes, Willow Grove; David A. Zopf, Strafford, all of PA (US)

(73) Assignee: Neose Technologies, Inc., Horsham, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/911,393

(22) Filed: Aug. 14, 1997

(51) Int. Cl.$^7$ .................................... C12P 19/26
(52) U.S. Cl. .................. 435/84; 435/99; 435/101; 435/274; 536/124; 536/127
(58) Field of Search ............... 435/101, 84, 99, 435/274; 536/124, 127

(56) References Cited

U.S. PATENT DOCUMENTS

| | | |
|---|---|---|
| 4,001,198 | 1/1977 | Thomas . |
| 4,202,909 | 5/1980 | Pederson . |
| 4,543,261 | 9/1985 | Harmon et al. . |
| 4,547,386 | 10/1985 | Chambers et al. . |
| 4,617,861 | 10/1986 | Armstrong . |
| 4,855,056 | 8/1989 | Harju et al. . |
| 4,873,316 | 10/1989 | Meade et al. . |
| 4,968,521 | 11/1990 | Melnychyn . |
| 4,971,701 | 11/1990 | Harju et al. . |
| 5,118,516 | 6/1992 | Shimatani et al. . |
| 5,164,374 | 11/1992 | Rademacher et al. . |
| 5,270,462 | 12/1993 | Shimatani et al. . |
| 5,330,975 | 7/1994 | Isoda et al. . |
| 5,374,541 | 12/1994 | Wong et al. . |
| 5,409,817 | 4/1995 | Ito et al. . |
| 5,514,660 | 5/1996 | Zopf et al. . |
| 5,575,916 | 11/1996 | Brian et al. . |
| 5,700,671 | 12/1997 | Prieto et al. . |

FOREIGN PATENT DOCUMENTS

| | | |
|---|---|---|
| 59-184197 | 10/1984 | (JP) . |
| 63-284199 | 11/1988 | (JP) . |
| WO 94/25616 | 11/1994 | (WO) . |
| WO 96/32491 | 10/1996 | (WO) . |
| WO 96/32492 | 10/1996 | (WO) . |

OTHER PUBLICATIONS

Scudder et al., 1993, "Enzymatic Characterization of β–D–Galactoside, α2,3–trans–Sialidase From *Trypanosoma cruzi*," J. Biol. Chem. 268(13):9886–9891.

Chuenkova et al., 1995, "*Trypanosoma cruzi* trans–Sialidase: Enhancement of Virulence in a Murine Model of Chagas' Disease," J. Exp. Med. 181:1693–1703.

Briones et al., 1995, "*Trypanosoma cruzi* trans–Sialidase Gene Lacking C–terminal Repeats and Expressed in Epimastigote Forms", Mol. & Biochemical Parasitol. 70:9–17.

Campetella et al., 1994, "A recombinant *Trypanosoma cruzi* trans–sialidase lacking the amino acid repeats retains the enzymatic activity", Mol. Biochem. Parasitol. 64:337–340.

Carver et al., 1993, "Transgenic livestock as bioreactors: Stable expression of human alpha–1–antirypsin by a flock of sheep", Biotechnol. 11:1263–1270.

Clark et al., 1989, "Expression of human anti–hemophilic factor IX in the milk of transgenic sheep," Biotechnol. 7:487–492.

Colli, W., 1993, "Trans–sialidase: A unique enzyme activity discovered in the protozoan *Trypanosoma cruzi*", FASEB J. 7:1257–1264.

Colman, A., 1996, "Production of proteins in the milk of transgenic livestock: Problems, solutions, and successes[1,2]," Am.J. Clin. Nutr. 63:639S–645S.

Cremona et al., 1995, "A single tyrosine differentiates active and inactive *Trypanosoma cruzi* trans–sialidases", Gene 160:123–128.

Cross et al., 1993, "The surface trans–sialidase family of *Trypanosoma cruzi*", Annu. Rev. Microbiol. 47:385–411.

Ebert et al., 1991, "Transgenic production of a variant of human tissue–type plasminogen activator in goat milk: Generation of transgenic goats and analysis of expression", Biotechnol. 9:835–838.

(List continued on next page.)

Primary Examiner—Francisco Prats
(74) Attorney, Agent, or Firm—Pennie & Edmonds LLP

(57) ABSTRACT

The present invention provides methods for producing sialyloligosaccharides in situ in dairy sources and cheese processing waste streams, prior to, during, or after processing of the dairy source during the cheese manufacturing process. The methods of the present invention use the catalytic activity of α(2-3) trans-sialidases to exploit the high concentrations of lactose and α(2-3) sialosides which naturally occur in dairy sources and cheese processing waste streams to drive the enzymatic synthesis of α(2-3) sialyllactose. α(2-3) sialyloligosaccharides produced according to these methods are additionally encompassed by the present invention. The invention also provides for recovery of the sialyloligosaccharides produced by these methods. The invention further provides a method for producing α(2-3) sialyllactose. The invention additionally provides a method of enriching for α(2-3) sialyllactose in milk using transgenic mammals that express an α(2-3) trans-sialidase transgene. The invention also provides for recovery of the sialyllactose contained in the milk produced by this transgenic mammal either before or after processing of the milk. Transgenic mammals containing an α(2-3) trans-sialidase encoding sequence operably linked to a regulatory sequence of a gene expressed in mammary tissue are also provided by the invention.

35 Claims, 7 Drawing Sheets

OTHER PUBLICATIONS

Figure 5:
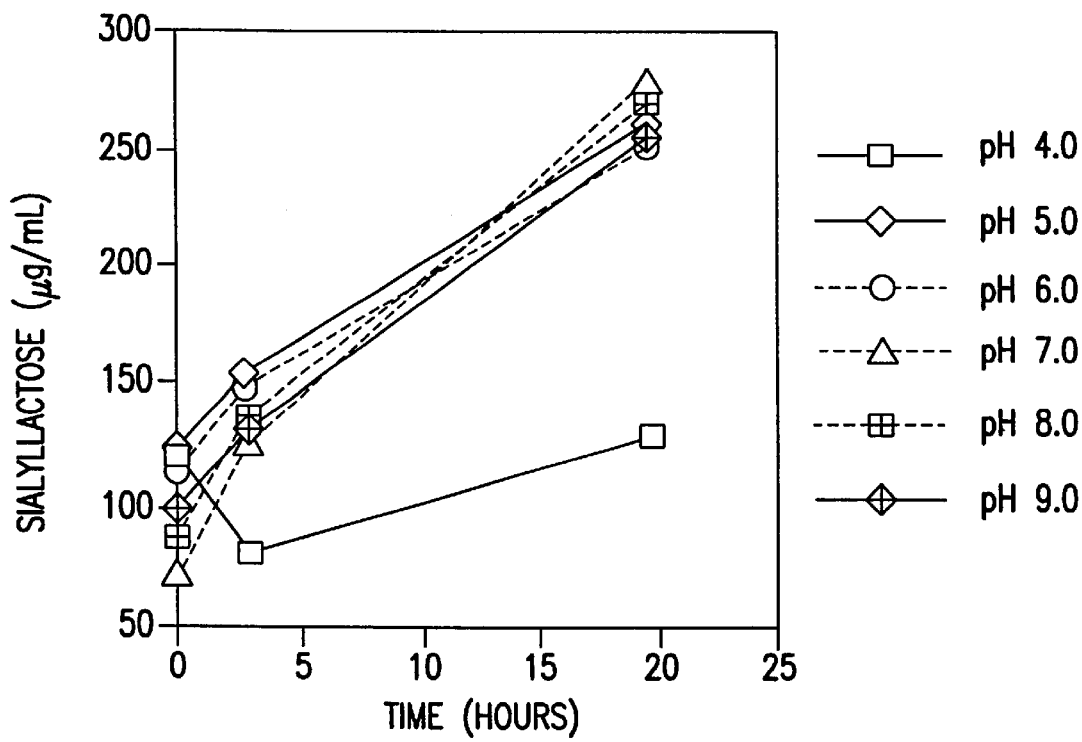

Houdebine, L., 1994, "Production of pharmaceutical proteins from transgenic animals", *J. Biotechnol.* 43:269–287.

Medina–Acosta et al., 1994, "Combined occurrence of trypanosomal sialidase/trans–sialidase activities and leishmanial metalloproteinase gene homologues in *Endotrypanum sp.*", *Mol. Biochem. Parasitol.* 64:273–282.

Paterson et al., 1994, "Approaches to maximizing stable expression of $\alpha_1$–antitrypsin in transformed CHO cells", *Appl. Microbiol. Biotechnol.* 40:691–698.

Pontes de Carvalho et al., 1993, "Characterization of a novel trans–sialidase of *Trypanosoma brucei* procyclic trypomastigotes and identification of procyclin as the main sialic acid acceptor", *J. Exp. Med.* 177:465–474.

Schenkman et al., 1992, "*Trypanosoma cruzi* trans–sialidase and neuraminidase activities can be mediated by the same enzymes", *J. Exp. Med.* 175:567–575.

Schenkman et al., 1994, "Structural and functional properties of Trypanosoma trans–sialidase", *Annu. Rev. Microbiol.* 48:499–523.

Schenkman et al., 1994, "A proteolytic fragment of *Trypanosoma cruzi* trans–sialidase lacking the carboxyl–terminal domain is active, monomeric, and generates antibodies that inhibit enzymatic activity*", *J. Biol. Chem.* 269:7970–7975.

Uemura et al., 1992, "Only some members of a gene family in *Trypanosoma cruzi* encode proteins that express both trans–sialidase and neuraminidase activities", *EMBO J.* 11:3837–3844.

Vandekerckhove et al., 1992, "Substrate specificity of the *Trypanosoma cruzi* trans–sialidase", *Glycobiiol.* 2:541–548.

Velander et al., 1992, "High–level expression of a heterologous protein in the milk of transgenic swine using the cDNA encoding human protein C", *Proc. Natl. Acad. Sci. USA* 89:12003–12007.

Wright et al., 1991, "High level expression of active human alpha–1–antitrypsin in the milk of transgenic sheep", *Biotechnol.* 9:830–834.

```
atggggaaaa cagtcgttgg ggccagtagg atgttctggc taatgttttt cgtgccgctt    60
cttcttgcgc tctgccccag cgagcccgcg catgccctgg cacccggatc gagccgagtt   120
gagctgttta agcggcaaag ctcgaaggtg ccatttgaaa agggcggcaa agtcaccgag   180
cgggttgtcc actcgttccg cctccccgcc cttgttaatg tggacggggt gatggttgcc   240
atcgcggacg ctcgctacga aacatccaat gacaactccc tcattgatac ggtggcgaag   300
tacagcgtgg acgatgggga gacgtgggag acccaaattg ccatcaagaa cagtcgtgca   360
tcgtctgttt ctcgtgtggt ggatcccaca gtgattgtga agggcaacaa gctttacgtc   420
ctggttggaa gctacaacag ttcgaggagc tactggacgt cgcatggtga tgcgagagac   480
tgggatattc tgcttgccgt tggtgaggtc acgaagtcca ctgcgggcgg caagataact   540
gcgagtatca aatgggggag ccccgtgtca ctgaaggaat ttttcccggc ggaaatggaa   600
ggaatgcaca caaatcaatt tcttggcggt gcaggtgttg ccattgtggc gtccaacggg   660
aatcttgtgt accctgtgca ggttacgaac aaaagaagc aagtttttc caagatcttc    720
tactcggaag acgagggcaa gacgtggaag tttggggagg gtaggagtga ttttggctgc   780
tctgaacctg tggcccttga gtgggagggg aagctcatca taaacactcg agttgactat   840
cgccgccgtc tggtgtacga gtccagtgac atggggaatt cgtgggtgga ggctgtcggc   900
acgctctcac gtgtgtgggg cccctcacca aaatcgaacc agcccggcag tcagagcagc   960
ttcactgccg tgaccatcga gggaatgcgt gttatgctct tcacacaccc gctgaatttt  1020
aagggaaggt ggctgcgcga ccgactgaac ctctggctga cggataacca gcgcatttat  1080
aacgttgggc aagtatccat tggtgatgaa aattccgcct acagctccgt cctgtacaag  1140
gatgataagc tgtactgttt gcatgagatc aacagtaacg aggtgtacag ccttgttttt  1200
gcgcgcctgg ttggcgagct acggatcatt aaatcagtgc tgcagtcctg gaagaattgg  1260
gacagccacc tgtccagcat ttgcacccct gctgatccag ccgcttcgtc gtcagagcgt  1320
ggttgtggtc ccgctgtcac cacggttggt cttgttggct ttttgtcgca cagtgccacc  1380
aaaaccgaat gggaggatgc gtaccgctgc gtcaacgcaa gcacggcaaa tgcggagagg  1440
gttccgaacg gtttgaagtt tgcggggggtt ggcggagggg cgctttggcc ggtgagccag  1500
caggggcaga ctcaacggta tcactttgca aaccacgcgt tcacgctggt ggcgtcggtg  1560
acgattcacg aggttccgag cgtcgcgagt cctttgctgg gtgcgagcct ggactcttct  1620
ggtggcaaaa aactcctggg gctctcgtac gacgagaagc accagtggca gccaatatac  1680
ggatcaacgc cggtgacgcc gaccggatcg tgggagatgg gtaagaggta ccacgtggtt  1740
cttacgatgg cgaataaaat tggttcggtg tacattgatg gagaacctct ggagggttca  1800
gggcagaccg ttgtgccaga cgggaggacg cctgacatct cccacttcta cgttggcggg  1860
tatggaagga gtgatatgcc aaccataagc cacgtgacgg tgaataatgt tcttctttac  1920
aaccgtcagc tgaatgccga ggagatcagg accttgttct tgagccagga cctgattggc  1980
acggaagcac acatgggcag cagcagcggc agcagtgccc acagtacgcc ctcaactccc  2040
gctgacaacg gtgcccacag tacgccctca actccgctg acagcagtgc ccacagtacg  2100
ccctcaactc cgctgacag cagtgcccac agtacgccct cagctcccgg tgacaacggt  2160
gcccacagta cgccctcgac tcccggtgac agcagtgccc acagtacgcc ctcaactccc  2220
gctgacaacg gtgcccacag tacgccctca gctcccgctg acagcaatgc ccacagtacg  2280
ccctcgactc cgctgacaa cggtgcccac agtacgccct caactcccgc tgacaacggt  2340
gcccacagta cgccctcgac tcccggtgac aacggtgccc acagtacgcc ctcgactccc  2400
ggtgacagca gtgcccacag tacgccctca actccgctg acaacggtgc cacagtacg   2460
ccctcagctc cgctgacag caatgcccac agtacgccct cgactccgg tgacaacggt   2520
gcccacagta cgccctcagc tcccgctgac agcaatgccc acagtacgcc ctcgactccc  2580
gctgacagca gtgcccacag tacgccctca gctcccggtg acaacggtgc cacagtacg   2640
ccctcagctc cgctgacag cagtgcccac agtacgccct cagctcccgg tgacaacggt   2700
gcccacagta cgccctcagc tcccgctgac aacggtgccc acagtacgcc ctcagctccc  2760
ggtgacagca atgcccacag tacgccctcg actccgctg acagcagtgc cacagtacg   2820
ccctcaactc cgctgacag cagtgcccac agtacgccct cagctcccgg tgacaacggt   2880
gcccacagta cgccctcagc tcccgctgac agcagtgccc acagtacgcc ctcaattccc  2940
ggtgacagca gtgcccacag tacgccctca gctcccgctg acagcagtca gcacagtca   3000
ccctcagctc cggtgacaa cggtgcccac agtacgccct cgactcccgc tgacaacggc  3060
gctaatggta cggttttgat tttgcacgat ggcgctgcat tttcggcctt tcgggcgga   3120
gggcttcttt tgtgtgcggg tgctttgctg ctgcacgtgt tcgttatggc agttttttc   3180
tga                                                                3183
```

FIG.1

MGKTVVGASRMFWLMFFVPLLLALCPSEPAHALAPGSSRVELFK
RQSSKVPFEKGGKVTERVVHSFRLPALVNVDGVMVAIADARYETSNDNSLIDTVAKYS
VDDGETWETQIAIKNSRASSVSRVVDPTVIVKGNKLYVLVGSYNSSRSYWTSHGDARD
WDILLAVGEVTKSTAGGKITASIKWGSPVSLKEFFPAEMEGMHTNQFLGGAGVAIVAS
NGNLVYPVQVTNKKKQVFSKIFYSEDEGKTWKFGEGRSDFGCSEPVALEWEGKLIINT
RVDYRRRLVYESSDMGNSWVEAVGTLSRVWGPSPKSNQPGSQSSFTAVTIEGMRVMLF
THPLNFKGRWLRDRLNLWLTDNQRIYNVGQVSIGDENSAYSSVLYKDDKLYCLHEINS
NEVYSLVFARLVGELRIIKSVLQSWKNWDSHLSSICTPADPAASSSERGCGPAVTTVG
LVGFLSHSATKTEWEDAYRCVNASTANAERVPNGLKFAGVGGGALWPVSQQGQNQRYH
FANHAFTLVASVTIHEVPSVASPLLGASLDSSGGKKLLGLSYDEKHQWQPIYGSTPVT
PTGSWEMGKRYHVVLTMANKIGSVYIDGEPLEGSGQTVVPDGRTPDISHFYVGGYGRS
DMPTISHVTVNNVLLYNRQLNAEEIRTLFLSQDLIGTEAHMGSSSGSSAHSTPSTPAD
NGAHSTPSTPADSSAHSTPSTPADSSAHSTPSAPGDNGAHSTPSTPGDSSAHSTPSTP
ADNGAHSTPSAPADSNAHSTPSTPADNGAHSTPSTPADNGAHSTPSTPGDNGAHSTPS
TPGDSSAHSTPSTPADNGAHSTPSAPADSNAHSTPSTPGDNGAHSTPSAPADSNAHST
PSTPADSSAHSTPSAPGDNGAHSTPSAPADSSAHSTPSAPGDNGAHSTPSAPADNGAH
STPSAPGDSNAHSTPSTPADSSAHSTPSTPADSSAHSTPSAPGDNGAHSTPSAPADSS
AHSTPSIPGDSSAHSTPSAPADSSAHSTPSAPGDNGAHSTPSTPADNGANGTVLILHD
GAAFSAFSGGGLLLCAGALLLHVFVMAVFF

FIG.2

```
atgctggcac ccggatagag ccgagttgag ctgtttaagc ggcaaagctc gaaggtgcca
tttgaaaagg acggcaaagt caccgagcgg gttgtccact cgttccgcct ccccgcccctt
gttaatgtgg acggggtgat ggttgccatc gcggacgctc gctacgaaac atccaatgac
aactccctca ttgatacggt ggcgaagtac agcgtggacg atggggagac gtgggagacc
caaattgcca tcaagaacag tcgtgcatcg tctgtttctc gtgtggtgga tcccacagtg
attgtgaagg gcaacaagct ttacgtcctg gttggaagct acaacagttc gaggagctac
tggacgtcgc atggtgatgc gagagactgg gatattctgc ttgccgttgg tgaggtcacg
aagtccactg cgggcggcaa gataactgcg agtatcaaat gggggagccc cgtgtcactg
aaggaatttt ttccggcgga atggaagga atgcacacaa atcaatttct tggcggtgca
ggtgttgcca ttgtggcgtc aacgggaat cttgtgtacc ctgtgcaggt tacgaacaaa
aagaagcaag ttttttccaa gatcttctac tcggaagacg agggcaagac gtggaagttt
gggaagggta ggagcgcttt tggctgctct gaacctgtgg cccttgagtg ggaggggaag
ctcatcataa acactcgagt tgactatcgc cgccgtctgg tgtacgagtc cagtgacatg
gggaattcgt ggctggaggc tgtcggcacg ctctcacgtg tgtggggccc ctcaccaaaa
tcgaaccagc ccggcagtca gagcagcttc actgccgtga ccatcgaggg aatgcgtgtt
atgctcttca cacacccgct gaattttaag ggaaggtggc tgcgcgaccg actgaacctc
tggctgacgg ataaccagcg catttataac gttgggcaag tatccattgg tgatgaaaat
tccgcctaca gctccgtcct gtacaaggat gataagctgt actgtttgca tgagatcaac
agtaacgagg tgtacagcct tgttttgcg cgcctggttg gcgagctacg gatcattaaa
tcagtgctgc agtcctggaa gaattgggac agccacctgt ccagcatttg cacccatgct
gatccagccg cttcgtcgtc agagcgtggt tgtggtcccg ctgtcaccac ggttggtctt
gttggctttt tgtcgcacag tgccaccaaa accgaatggg aggatgcgta ccgctgcgtg
aacgcaagca cggcaaatgc ggagagggtt ccgaacggtt tgaagtttgc ggggggttggc
ggaggggcgc tttggccggt gagccagcag gggcagaatc aacggtatcg ctttgcaaac
cacgcgttca ccgtggtggc gtcggtgacg attcacgagg ttccgagcgt cgcgagtcct
ttgctgggtg cgagcctgga ctcttctggt ggcaaaaaac tcctggggct ctcgtacgac
gagaggcacc agtggcagcc aatatacgga tcaacgccgg tgacgccgac cggatcgtgg
gagatgggta agaggtacca cgtggttctt acgatggcga ataaaattgg ctccgagtac
attgatggag aacctctgga ggggttcaggg cagaccgttg tgccagacga gaggacgcct
gacatctccc acttctacgt tggcgggtat aaaaggagtg atatgccaac cataagccac
gtgacggtga ataatgttct tctttacaac cgtcagctga atgccgagga gatcaggacc
ttgttcttga gccaggacct gattggcacg gaagcacaca tggacagcag cagcgacacg
agtgcctga
```

FIG.3

```
                    MLAPGSSRVELFKRQSSKVPFEKDGKVTERVVHSFRLPALVNVD
GVMVAIADARYETSNDNSLIDTVAKYSVDDGETWETQIAIKNSRASSVSRVVDPTVIV
KGNKLYVLVGSYNSSRSYWTSHGDARDWDILLAVGEVTKSTAGGKITASIKWGSPVSL
KEFFPAEMEGMHTNQFLGGAGVAIVASNGNLVYPVQVTNKKKQVFSKIFYSEDEGKTW
KFGKGRSAFGCSEPVALEWEGKLIINTRVDYRRRLVYESSDMGNSWLEAVGTLSRVWG
PSPKSNQPGSQSSFTAVTIEGMRVMLFTHPLNFKGRWLRDRLNLWLTDNQRIYNVGQV
SIGDENSAYSSVLYKDDKLYCLHEINSNEVYSLVFARLVGELRIIKSVLQSWKNWDSH
LSSICTPADPAASSSERGCGPAVTTVGLVGFLSHSATKTEWEDAYRCVNASTANAERV
PNGLKFAGVGGGALWPVSQQGQNQRYRFANHAFTVVASVTIHEVPSVASPLLGASLDS
SGGKKLLGLSYDERHQWQPIYGSTPVTPTGSWEMGKRYHVVLTMANKIGSEYIDGEPL
EGSGQTVVPDERTPDISHFYVGGYKRSDMPTISHVTVNNVLLYNRQLNAEEIRTLFLS
QDLIGTEAHMDSSSDTSA
```

FIG.4

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 3183 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
ATGGGGAAAA CAGTCGTTGG GGCCAGTAGG ATGTTCTGGC TAATGTTTTT CGTGCCGCTT      60

CTTCTTGCGC TCTGCCCCAG CGAGCCCGCG CATGCCCTGG CACCCGGATC GAGCCGAGTT     120
```

```
GAGCTGTTTA AGCGGCAAAG CTCGAAGGTG CCATTTGAAA AGGGCGGCAA AGTCACCGAG    180

CGGGTTGTCC ACTCGTTCCG CCTCCCCGCC CTTGTTAATG TGGACGGGGT GATGGTTGCC    240

ATCGCGGACG CTCGCTACGA AACATCCAAT GACAACTCCC TCATTGATAC GGTGGCGAAG    300

TACAGCGTGG ACGATGGGGA GACGTGGGAG ACCCAAATTG CCATCAAGAA CAGTCGTGCA    360

TCGTCTGTTT CTCGTGTGGT GGATCCCACA GTGATTGTGA AGGGCAACAA GCTTTACGTC    420

CTGGTTGGAA GCTACAACAG TTCGAGGAGC TACTGGACGT CGCATGGTGA TGCGAGAGAC    480

TGGGATATTC TGCTTGCCGT TGGTGAGGTC ACGAAGTCCA CTGCGGGCGG CAAGATAACT    540

GCGAGTATCA AATGGGGGAG CCCCGTGTCA CTGAAGGAAT TTTTCCCGGC GGAAATGGAA    600

GGAATGCACA CAAATCAATT TCTTGGCGGT GCAGGTGTTG CCATTGTGGC GTCCAACGGG    660

AATCTTGTGT ACCCTGTGCA GGTTACGAAC AAAAAGAAGC AAGTTTTTTC CAAGATCTTC    720

TACTCGGAAG ACGAGGGCAA GACGTGGAAG TTTGGGGAGG GTAGGAGTGA TTTTGGCTGC    780

TCTGAACCTG TGGCCCTTGA GTGGGAGGGG AAGCTCATCA TAAACACTCG AGTTGACTAT    840

CGCCGCCGTC TGGTGTACGA GTCCAGTGAC ATGGGGAATT CGTGGGTGGA GGCTGTCGGC    900

ACGCTCTCAC GTGTGTGGGG CCCCTCACCA AAATCGAACC AGCCCGGCAG TCAGAGCAGC    960

TTCACTGCCG TGACCATCGA GGGAATGCGT GTTATGCTCT TCACACACCC GCTGAATTTT   1020

AAGGGAAGGT GGCTGCGCGA CCGACTGAAC CTCTGGCTGA CGGATAACCA GCGCATTTAT   1080

AACGTTGGGC AAGTATCCAT TGGTGATGAA AATTCCGCCT ACAGCTCCGT CCTGTACAAG   1140

GATGATAAGC TGTACTGTTT GCATGAGATC AACAGTAACG AGGTGTACAG CCTTGTTTTT   1200

GCGCGCCTGG TTGGCGAGCT ACGGATCATT AAATCAGTGC TGCAGTCCTG GAAGAATTGG   1260

GACAGCCACC TGTCCAGCAT TTGCACCCCT GCTGATCCAG CCGCTTCGTC GTCAGAGCGT   1320

GGTTGTGGTC CCGCTGTCAC CACGGTTGGT CTTGTTGGCT TTTTGTCGCA CAGTGCCACC   1380

AAAACCGAAT GGGAGGATGC GTACCGCTGC GTCAACGCAA GCACGGCAAA TGCGGAGAGG   1440

GTTCCGAACG GTTTGAAGTT TGCGGGGGTT GGCGGAGGGG CGCTTTGGCC GGTGAGCCAG   1500

CAGGGGCAGA ATCAACGGTA TCACTTTGCA AACCACGCGT TCACGCTGGT GGCGTCGGTG   1560

ACGATTCACG AGGTTCCGAG CGTCGCGAGT CCTTTGCTGG GTGCGAGCCT GGACTCTTCT   1620

GGTGGCAAAA AACTCCTGGG GCTCTCGTAC GACGAGAAGC ACCAGTGGCA GCCAATATAC   1680

GGATCAACGC CGGTGACGCC GACCGGATCG TGGGAGATGG GTAAGAGGTA CCACGTGGTT   1740

CTTACGATGG CGAATAAAAT TGGTTCGGTG TACATTGATG GAGAACCTCT GGAGGGTTCA   1800

GGGCAGACCG TTGTGCCAGA CGGGAGGACG CCTGACATCT CCCACTTCTA CGTTGGCGGG   1860

TATGGAAGGA GTGATATGCC AACCATAAGC CACGTGACGG TGAATAATGT TCTTCTTTAC   1920

AACCGTCAGC TGAATGCCGA GGAGATCAGG ACCTTGTTCT TGAGCCAGGA CCTGATTGGC   1980

ACGGAAGCAC ACATGGGCAG CAGCAGCGGC AGCAGTGCCC ACAGTACGCC CTCAACTCCC   2040

GCTGACAACG GTGCCCACAG TACGCCCTCA ACTCCGCTG ACAGCAGTGC CCACAGTACG   2100

CCCTCAACTC CCGCTGACAG CAGTGCCCAC AGTACGCCCT CAGCTCCCGG TGACAACGGT   2160

GCCCACAGTA CGCCCTCGAC TCCCGGTGAC AGCAGTGCCC ACAGTACGCC CTCAACTCCC   2220

GCTGACAACG GTGCCCACAG TACGCCCTCA GCTCCCGCTG ACAGCAATGC CCACAGTACG   2280

CCCTCGACTC CCGCTGACAA CGGTGCCCAC AGTACGCCCT CAACTCCCGC TGACAACGGT   2340

GCCCACAGTA CGCCCTCGAC TCCCGGTGAC AACGGTGCCC ACAGTACGCC CTCGACTCCC   2400

GGTGACAGCA GTGCCCACAG TACGCCCTCA ACTCCGCTG ACAACGGTGC CCACAGTACG   2460
```

-continued

```
CCCTCAGCTC CCGCTGACAG CAATGCCCAC AGTACGCCCT CGACTCCCGG TGACAACGGT    2520

GCCCACAGTA CGCCCTCAGC TCCCGCTGAC AGCAATGCCC ACAGTACGCC CTCGACTCCC    2580

GCTGACAGCA GTGCCCACAG TACGCCCTCA GCTCCCGGTG ACAACGGTGC CCACAGTACG    2640

CCCTCAGCTC CCGCTGACAG CAGTGCCCAC AGTACGCCCT CAGCTCCCGG TGACAACGGT    2700

GCCCACAGTA CGCCCTCAGC TCCCGCTGAC AACGGTGCCC ACAGTACGCC CTCAGCTCCC    2760

GGTGACAGCA ATGCCCACAG TACGCCCTCG ACTCCCGCTG ACAGCAGTGC CCACAGTACG    2820

CCCTCAACTC CCGCTGACAG CAGTGCCCAC AGTACGCCCT CAGCTCCCGG TGACAACGGT    2880

GCCCACAGTA CGCCCTCAGC TCCCGCTGAC AGCAGTGCCC ACAGTACGCC CTCAATTCCC    2940

GGTGACAGCA GTGCCCACAG TACGCCCTCA GCTCCCGCTG ACAGCAGTGC CCACAGTACG    3000

CCCTCAGCTC CCGGTGACAA CGGTGCCCAC AGTACGCCCT CGACTCCCGC TGACAACGGC    3060

GCTAATGGTA CGGTTTTGAT TTTGCACGAT GGCGCTGCAT TTTCGGCCTT TCGGGCGGA    3120

GGGCTTCTTT TGTGTGCGGG TGCTTTGCTG CTGCACGTGT TCGTTATGGC AGTTTTTTTC    3180

TGA                                                                 3183
```

(2) INFORMATION FOR SEQ ID NO:2:

(i) SEQUENCE CHARACTERISTICS:
        (A) LENGTH: 1060 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Gly Lys Thr Val Gly Ala Ser Arg Met Phe Trp Leu Met Phe
 1               5                  10                  15

Phe Val Pro Leu Leu Ala Leu Cys Pro Ser Glu Pro Ala His Ala
             20                  25                  30

Leu Ala Pro Gly Ser Ser Arg Val Glu Leu Phe Lys Arg Gln Ser Ser
         35                  40                  45

Lys Val Pro Phe Glu Lys Gly Gly Lys Val Thr Glu Arg Val Val His
     50                  55                  60

Ser Phe Arg Leu Pro Ala Leu Val Asn Val Asp Gly Val Met Val Ala
65                  70                  75                  80

Ile Ala Asp Ala Arg Tyr Glu Thr Ser Asn Asp Asn Ser Leu Ile Asp
                 85                  90                  95

Thr Val Ala Lys Tyr Ser Val Asp Asp Gly Glu Thr Trp Glu Thr Gln
            100                 105                 110

Ile Ala Ile Lys Asn Ser Arg Ala Ser Ser Val Ser Arg Val Val Asp
        115                 120                 125

Pro Thr Val Ile Val Lys Gly Asn Lys Leu Tyr Val Leu Val Gly Ser
    130                 135                 140

Tyr Asn Ser Ser Arg Ser Tyr Trp Thr Ser His Gly Asp Ala Arg Asp
145                 150                 155                 160

Trp Asp Ile Leu Leu Ala Val Gly Glu Val Thr Lys Ser Thr Ala Gly
                165                 170                 175

Gly Lys Ile Thr Ala Ser Ile Lys Trp Gly Ser Pro Val Ser Leu Lys
            180                 185                 190

Glu Phe Phe Pro Ala Glu Met Glu Gly Met His Thr Asn Gln Phe Leu
        195                 200                 205

Gly Gly Ala Gly Val Ala Ile Val Ala Ser Asn Gly Asn Leu Val Tyr
```

-continued

```
               210                 215                 220
Pro Val Gln Val Thr Asn Lys Lys Gln Val Phe Ser Lys Ile Phe
225                 230                 235                 240
Tyr Ser Glu Asp Glu Gly Lys Thr Trp Lys Phe Gly Glu Gly Arg Ser
                245                 250                 255
Asp Phe Gly Cys Ser Glu Pro Val Ala Leu Glu Trp Glu Gly Lys Leu
                260                 265                 270
Ile Ile Asn Thr Arg Val Asp Tyr Arg Arg Arg Leu Val Tyr Glu Ser
                275                 280                 285
Ser Asp Met Gly Asn Ser Trp Val Glu Ala Val Gly Thr Leu Ser Arg
290                 295                 300
Val Trp Gly Pro Ser Pro Lys Ser Asn Gln Pro Gly Ser Gln Ser Ser
305                 310                 315                 320
Phe Thr Ala Val Thr Ile Glu Gly Met Arg Val Met Leu Phe Thr His
                325                 330                 335
Pro Leu Asn Phe Lys Gly Arg Trp Leu Arg Asp Arg Leu Asn Leu Trp
                340                 345                 350
Leu Thr Asp Asn Gln Arg Ile Tyr Asn Val Gly Gln Val Ser Ile Gly
                355                 360                 365
Asp Glu Asn Ser Ala Tyr Ser Ser Val Leu Tyr Lys Asp Asp Lys Leu
370                 375                 380
Tyr Cys Leu His Glu Ile Asn Ser Asn Glu Val Tyr Ser Leu Val Phe
385                 390                 395                 400
Ala Arg Leu Val Gly Glu Leu Arg Ile Ile Lys Ser Val Leu Gln Ser
                405                 410                 415
Trp Lys Asn Trp Asp Ser His Leu Ser Ser Ile Cys Thr Pro Ala Asp
                420                 425                 430
Pro Ala Ala Ser Ser Ser Glu Arg Gly Cys Gly Pro Ala Val Thr Thr
                435                 440                 445
Val Gly Leu Val Gly Phe Leu Ser His Ser Ala Thr Lys Thr Glu Trp
                450                 455                 460
Glu Asp Ala Tyr Arg Cys Val Asn Ala Ser Thr Ala Asn Ala Glu Arg
465                 470                 475                 480
Val Pro Asn Gly Leu Lys Phe Ala Gly Val Gly Gly Gly Ala Leu Trp
                485                 490                 495
Pro Val Ser Gln Gln Gly Gln Asn Gln Arg Tyr His Phe Ala Asn His
                500                 505                 510
Ala Phe Thr Leu Val Ala Ser Val Thr Ile His Glu Val Pro Ser Val
                515                 520                 525
Ala Ser Pro Leu Leu Gly Ala Ser Leu Asp Ser Ser Gly Gly Lys Lys
530                 535                 540
Leu Leu Gly Leu Ser Tyr Asp Glu Lys His Gln Trp Gln Pro Ile Tyr
545                 550                 555                 560
Gly Ser Thr Pro Val Thr Pro Thr Gly Ser Trp Glu Met Gly Lys Arg
                565                 570                 575
Tyr His Val Val Leu Thr Met Ala Asn Lys Ile Gly Ser Val Tyr Ile
                580                 585                 590
Asp Gly Glu Pro Leu Glu Gly Ser Gly Gln Thr Val Val Pro Asp Gly
                595                 600                 605
Arg Thr Pro Asp Ile Ser His Phe Tyr Val Gly Gly Tyr Gly Arg Ser
                610                 615                 620
Asp Met Pro Thr Ile Ser His Val Thr Val Asn Asn Val Leu Leu Tyr
625                 630                 635                 640
```

-continued

```
Asn Arg Gln Leu Asn Ala Glu Glu Ile Arg Thr Leu Phe Leu Ser Gln
                645                 650                 655
Asp Leu Ile Gly Thr Glu Ala His Met Gly Ser Ser Gly Ser Ser
            660                 665                 670
Ala His Ser Thr Pro Ser Thr Pro Ala Asp Asn Gly Ala His Ser Thr
        675                 680                 685
Pro Ser Thr Pro Ala Asp Ser Ser Ala His Ser Thr Pro Ser Thr Pro
    690                 695                 700
Ala Asp Ser Ser Ala His Ser Thr Pro Ser Ala Pro Gly Asp Asn Gly
705                 710                 715                 720
Ala His Ser Thr Pro Ser Thr Pro Gly Asp Ser Ser Ala His Ser Thr
            725                 730                 735
Pro Ser Thr Pro Ala Asp Asn Gly Ala His Ser Thr Pro Ser Ala Pro
        740                 745                 750
Ala Asp Ser Asn Ala His Ser Thr Pro Ser Thr Pro Ala Asp Asn Gly
    755                 760                 765
Ala His Ser Thr Pro Ser Thr Pro Ala Asp Asn Gly Ala His Ser Thr
770                 775                 780
Pro Ser Thr Pro Gly Asp Asn Gly Ala His Ser Thr Pro Ser Thr Pro
785             790                 795                 800
Gly Asp Ser Ser Ala His Ser Thr Pro Ser Thr Pro Ala Asp Asn Gly
            805                 810                 815
Ala His Ser Thr Pro Ser Ala Pro Ala Asp Ser Asn Ala His Ser Thr
        820                 825                 830
Pro Ser Thr Pro Gly Asp Asn Gly Ala His Ser Thr Pro Ser Ala Pro
    835                 840                 845
Ala Asp Ser Asn Ala His Ser Thr Pro Ser Thr Pro Ala Asp Ser Ser
    850                 855                 860
Ala His Ser Thr Pro Ser Ala Pro Gly Asp Asn Gly Ala His Ser Thr
865                 870                 875                 880
Pro Ser Ala Pro Ala Asp Ser Ser Ala His Ser Thr Pro Ser Ala Pro
            885                 890                 895
Gly Asp Asn Gly Ala His Ser Thr Pro Ser Ala Pro Ala Asp Asn Gly
        900                 905                 910
Ala His Ser Thr Pro Ser Ala Pro Gly Asp Ser Asn Ala His Ser Thr
    915                 920                 925
Pro Ser Thr Pro Ala Asp Ser Ser Ala His Ser Thr Pro Ser Thr Pro
    930                 935                 940
Ala Asp Ser Ser Ala His Ser Thr Pro Ser Ala Pro Gly Asp Asn Gly
945                 950                 955                 960
Ala His Ser Thr Pro Ser Ala Pro Ala Asp Ser Ser Ala His Ser Thr
            965                 970                 975
Pro Ser Ile Pro Gly Asp Ser Ser Ala His Ser Thr Pro Ser Ala Pro
        980                 985                 990
Ala Asp Ser Ser Ala His Ser Thr Pro Ser Ala Pro Gly Asp Asn Gly
    995                 1000                1005
Ala His Ser Thr Pro Ser Thr Pro Ala Asp Asn Gly Ala Asn Gly Thr
    1010                1015                1020
Val Leu Ile Leu His Asp Gly Ala Ala Phe Ser Ala Phe Ser Gly Gly
1025            1030                1035                1040
Gly Leu Leu Leu Cys Ala Gly Ala Leu Leu Leu His Val Phe Val Met
                1045                1050                1055
```

Ala Val Phe Phe
      1060

(2) INFORMATION FOR SEQ ID NO:3:

(i) SEQUENCE CHARACTERISTICS:
        (A) LENGTH: 1929 base pairs
        (B) TYPE: nucleic acid
        (C) STRANDEDNESS: unknown
        (D) TOPOLOGY: linear (ii) MOLECULE TYPE: cDNA (xi) SEQUENCE DESCRIPTION: SEQ ID NO:3:

```
ATGCTGGCAC CCGGATCGAG CCGAGTTGAG CTGTTTAAGC GGCAAAGCTC GAAGGTGCCA      60
TTTGAAAAGG ACGGCAAAGT CACCGAGCGG GTTGTCCACT CGTTCCGCCT CCCCGCCCTT     120
GTTAATGTGG ACGGGGTGAT GGTTGCCATC GCGGACGCTC GCTACGAAAC ATCCAATGAC     180
AACTCCCTCA TTGATACGGT GGCGAAGTAC AGCGTGGACG ATGGGGAGAC GTGGGAGACC     240
CAAATTGCCA TCAAGAACAG TCGTGCATCG TCTGTTTCTC GTGTGGTGGA TCCCACAGTG     300
ATTGTGAAGG GCAACAAGCT TTACGTCCTG GTTGGAAGCT ACAACAGTTC GAGGAGCTAC     360
TGGACGTCGC ATGGTGATGC GAGAGACTGG GATATTCTGC TTGCCGTTGG TGAGGTCACG     420
AAGTCCACTG CGGGCGGCAA GATAACTGCG AGTATCAAAT GGGGGAGCCC CGTGTCACTG     480
AAGGAATTTT TTCCGGCGGA AATGGAAGGA ATGCACACAA TCAATTTCT TGGCGGTGCA      540
GGTGTTGCCA TTGTGGCGTC CAACGGGAAT CTTGTGTACC CTGTGCAGGT TACGAACAAA     600
AAGAAGCAAG TTTTTTCCAA GATCTTCTAC TCGGAAGACG AGGGCAAGAC GTGGAAGTTT     660
GGGAAGGGTA GGAGCGCTTT TGGCTGCTCT GAACCTGTGG CCCTTGAGTG GGAGGGGAAG     720
CTCATCATAA ACACTCGAGT TGACTATCGC CGCCGTCTGG TGTACGAGTC CAGTGACATG     780
GGGAATTCGT GGCTGGAGGC TGTCGGCACG CTCTCACGTG TGTGGGGCCC CTCACCAAAA     840
TCGAACCAGC CCGGCAGTCA GAGCAGCTTC ACTGCCGTGA CCATCGAGGG AATGCGTGTT     900
ATGCTCTTCA CACACCCGCT GAATTTTAAG GGAAGGTGGC TGCGCGACCG ACTGAACCTC     960
TGGCTGACGG ATAACCAGCG CATTTATAAC GTTGGGCAAG TATCCATTGG TGATGAAAAT    1020
TCCGCCTACA GCTCCGTCCT GTACAAGGAT GATAAGCTGT ACTGTTTGCA TGAGATCAAC    1080
AGTAACGAGG TGTACAGCCT TGTTTTTGCG CGCCTGGTTG GCGAGCTACG GATCATTAAA    1140
TCAGTGCTGC AGTCCTGGAA GAATTGGGAC AGCCACCTGT CCAGCATTTG CACCCCTGCT    1200
GATCCAGCCG CTTCGTCGTC AGAGCGTGGT TGTGGTCCCG CTGTCACCAC GGTTGGTCTT    1260
GTTGGCTTTT TGTCGCACAG TGCCACCAAA ACCGAATGGG AGGATGCGTA CCGCTGCGTG    1320
AACGCAAGCA CGGCAAATGC GGAGAGGGTT CCGAACGGTT TGAAGTTTGC GGGGGTTGGC    1380
GGAGGGGCGC TTTGGCCGGT GAGCCAGCAG GGGCAGAATC AACGGTATCG CTTTGCAAAC    1440
CACGCGTTCA CCGTGGTGGC GTCGGTGACG ATTCACGAGG TTCCGAGCGT CGCGAGTCCT    1500
TTGCTGGGTG CGAGCCTGGA CTCTTCTGGT GGCAAAAAAC TCCTGGGGCT CTCGTACGAC    1560
GAGAGGCACC AGTGGCAGCC AATATACGGA TCAACGCCGG TGACGCCGAC CGGATCGTGG    1620
GAGATGGGTA AGAGGTACCA CGTGGTTCTT ACGATGGCGA ATAAAATTGG CTCCGAGTAC    1680
ATTGATGGAG AACCTCTGGA GGGTTCAGGG CAGACCGTTG TGCCAGACGA GAGGACGCCT    1740
GACATCTCCC ACTTCTACGT TGGCGGGTAT AAAAGGAGTG ATATGCCAAC CATAAGCCAC    1800
GTGACGGTGA ATAATGTTCT TCTTTACAAC CGTCAGCTGA ATGCCGAGGA GATCAGGACC    1860
TTGTTCTTGA GCCAGGACCT GATTGGCACG GAAGCACACA TGGACAGCAG CAGCGACACG    1920
```

AGTGCCTGA                                                                1929

(2) INFORMATION FOR SEQ ID NO:4:

(i) SEQUENCE CHARACTERISTICS:
        (A) LENGTH: 642 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Leu Ala Pro Gly Ser Ser Arg Val Glu Leu Phe Lys Arg Gln Ser
 1               5                  10                  15

Ser Lys Val Pro Phe Glu Lys Asp Gly Lys Val Thr Glu Arg Val Val
                20                  25                  30

His Ser Phe Arg Leu Pro Ala Leu Val Asn Val Asp Gly Val Met Val
                35                  40                  45

Ala Ile Ala Asp Ala Arg Tyr Glu Thr Ser Asn Asp Asn Ser Leu Ile
            50                  55                  60

Asp Thr Val Ala Lys Tyr Ser Val Asp Asp Gly Glu Thr Trp Glu Thr
65                  70                  75                  80

Gln Ile Ala Ile Lys Asn Ser Arg Ala Ser Val Ser Arg Val Val
                85                  90                  95

Asp Pro Thr Val Ile Val Lys Gly Asn Lys Leu Tyr Val Leu Val Gly
                100                 105                 110

Ser Tyr Asn Ser Ser Arg Ser Tyr Trp Thr Ser His Gly Asp Ala Arg
                115                 120                 125

Asp Trp Asp Ile Leu Leu Ala Val Gly Glu Val Thr Lys Ser Thr Ala
            130                 135                 140

Gly Gly Lys Ile Thr Ala Ser Ile Lys Trp Gly Ser Pro Val Ser Leu
145                 150                 155                 160

Lys Glu Phe Phe Pro Ala Glu Met Glu Gly Met His Thr Asn Gln Phe
                165                 170                 175

Leu Gly Gly Ala Gly Val Ala Ile Val Ala Ser Asn Gly Asn Leu Val
                180                 185                 190

Tyr Pro Val Gln Val Thr Asn Lys Lys Gln Val Phe Ser Lys Ile
                195                 200                 205

Phe Tyr Ser Glu Asp Glu Gly Lys Thr Trp Lys Phe Gly Lys Gly Arg
            210                 215                 220

Ser Ala Phe Gly Cys Ser Glu Pro Val Ala Leu Glu Trp Glu Gly Lys
225                 230                 235                 240

Leu Ile Ile Asn Thr Arg Val Asp Tyr Arg Arg Leu Val Tyr Glu
                245                 250                 255

Ser Ser Asp Met Gly Asn Ser Trp Leu Glu Ala Val Gly Thr Leu Ser
                260                 265                 270

Arg Val Trp Gly Pro Ser Pro Lys Ser Asn Gln Pro Gly Ser Gln Ser
                275                 280                 285

Ser Phe Thr Ala Val Thr Ile Glu Gly Met Arg Val Met Leu Phe Thr
                290                 295                 300

His Pro Leu Asn Phe Lys Gly Arg Trp Leu Arg Asp Arg Leu Asn Leu
305                 310                 315                 320

Trp Leu Thr Asp Asn Gln Arg Ile Tyr Asn Val Gly Gln Val Ser Ile
                325                 330                 335
```

```
Gly Asp Glu Asn Ser Ala Tyr Ser Ser Val Leu Tyr Lys Asp Asp Lys
            340                 345                 350

Leu Tyr Cys Leu His Glu Ile Asn Ser Asn Glu Val Tyr Ser Leu Val
            355                 360                 365

Phe Ala Arg Leu Val Gly Glu Leu Arg Ile Ile Lys Ser Val Leu Gln
            370                 375                 380

Ser Trp Lys Asn Trp Asp Ser His Leu Ser Ser Ile Cys Thr Pro Ala
385                 390                 395                 400

Asp Pro Ala Ala Ser Ser Glu Arg Gly Cys Gly Pro Ala Val Thr
                405                 410                 415

Thr Val Gly Leu Val Gly Phe Leu Ser His Ser Ala Thr Lys Thr Glu
            420                 425                 430

Trp Glu Asp Ala Tyr Arg Cys Val Asn Ala Ser Thr Ala Asn Ala Glu
            435                 440                 445

Arg Val Pro Asn Gly Leu Lys Phe Ala Gly Val Gly Gly Gly Ala Leu
            450                 455                 460

Trp Pro Val Ser Gln Gln Gly Gln Asn Gln Arg Tyr Arg Phe Ala Asn
465                 470                 475                 480

His Ala Phe Thr Val Val Ala Ser Val Thr Ile His Glu Val Pro Ser
            485                 490                 495

Val Ala Ser Pro Leu Leu Gly Ala Ser Leu Asp Ser Ser Gly Gly Lys
            500                 505                 510

Lys Leu Leu Gly Leu Ser Tyr Asp Glu Arg His Gln Trp Gln Pro Ile
            515                 520                 525

Tyr Gly Ser Thr Pro Val Thr Pro Thr Gly Ser Trp Glu Met Gly Lys
            530                 535                 540

Arg Tyr His Val Val Leu Thr Met Ala Asn Lys Ile Gly Ser Glu Tyr
545                 550                 555                 560

Ile Asp Gly Glu Pro Leu Glu Gly Ser Gly Gln Thr Val Val Pro Asp
            565                 570                 575

Glu Arg Thr Pro Asp Ile Ser His Phe Tyr Val Gly Gly Tyr Lys Arg
            580                 585                 590

Ser Asp Met Pro Thr Ile Ser His Val Thr Val Asn Asn Val Leu Leu
            595                 600                 605

Tyr Asn Arg Gln Leu Asn Ala Glu Glu Ile Arg Thr Leu Phe Leu Ser
            610                 615                 620

Gln Asp Leu Ile Gly Thr Glu Ala His Met Asp Ser Ser Ser Asp Thr
625                 630                 635                 640

Ser Ala (2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: Other (xi) SEQUENCE DESCRIPTION: SEQ ID NO:5:

TTTTCTAGAA TGCTGGCACC CGGATCGAGC                                30

(2) INFORMATION FOR SEQ ID NO:6:

(i) SEQUENCE CHARACTERISTICS:
        (A) LENGTH: 30 base pairs
```

-continued (B) TYPE: nucleic acid
        (C) STRANDEDNESS: unknown
        (D) TOPOLOGY: unknown (ii) MOLECULE TYPE: Other (xi) SEQUENCE DESCRIPTION: SEQ ID NO:6:

CTGTGCGACA AAAAGCCAAC AAGACCAACC                                    30

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: unknown
        (D) TOPOLOGY: unknown (ii) MOLECULE TYPE: Other (xi) SEQUENCE DESCRIPTION: SEQ ID NO:7:

ACTGAACCTC TGGCTGACGG ATAACCAGC                                     29

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: Other (xi) SEQUENCE DESCRIPTION: SEQ ID NO:8:

TTTCTCGAGT CAGGCACTCG TGTCGCTGCT                                    30

(2) INFORMATION FOR SEQ ID NO:9:

(i) SEQUENCE CHARACTERISTICS:
        (A) LENGTH: 40 base pairs
        (B) TYPE: nucleic acid
        (C) STRANDEDNESS: unknown
        (D) TOPOLOGY: unknown (ii) MOLECULE TYPE: Other (xi) SEQUENCE DESCRIPTION: SEQ ID NO:9:

GGGCAAGTAT CCATTGGTGA TGAAAATTCC GCCTACAGCT                          40

(2) INFORMATION FOR SEQ ID NO:10:

(i) SEQUENCE CHARACTERISTICS:
        (A) LENGTH: 40 base pairs
        (B) TYPE: nucleic acid
        (C) STRANDEDNESS: unknown
        (D) TOPOLOGY: unknown (ii) MOLECULE TYPE: Other (xi) SEQUENCE DESCRIPTION: SEQ ID NO:10:

TACAGCTTAT CATCCTTGTA CAGGACGGAG CTGTAGGCGG                          40

METHODS FOR PRODUCING SIALYLOLIGOSACCHARIDES IN A DAIRY SOURCE

1. INTRODUCTION

This invention relates to methods for producing α(2-3) sialyloligosaccharides in a dairy source or cheese processing waste stream by contacting the dairy source or cheese processing waste stream with a catalytic amount of at least one α(2-3) trans-sialidase. In preferred embodiments, the methods of the invention are applied to produce α(2-3) sialyllactose in a dairy source or cheese processing waste stream. Methods for isolating the α(2-3) sialyloligosaccharides produced according to the methods of the invention are also provided. The invention additionally relates to a method for producing α(2-3) sialyllactose in milk using a transgenic mammal containing an α(2-3) trans-sialidase encoding sequence operably linked to a regulatory sequence of a gene expressed in mammary tissue.

2. BACKGROUND OF THE INVENTION

2.1. Sialyloligosaccharides in Cheese Waste Streams

Whey is a major by-product of cheese manufacturing, which, for environmental reasons, presents a difficult waste disposal problem. In the United States alone, fluid whey is being produced at a rate of about 62.6 billion pounds annually. Whey is typically composed of about 5 wt. % lactose, 1 wt. % protein and about 0.5 wt. % salts, where the balance of the mixture is water. A major effort by many cheese making countries is presently underway to develop uses for this commodity, which formerly was considered a cheese processing waste product.

Although the protein concentrate obtained by ultrafiltration of whey has become a valuable commodity in the food industry and has found applications in animal feed, fertilizer, fermentation, and food filler, the majority of the resulting lactose-rich ultrafiltered permeate is still considered a disposable fraction.

Recently, several sialyloligosaccharides have been found to have valuable application as pharmaceutics. See, e.g. U.S. Pat. No. 5,270,462 to Shimatani et al. Sialyllactose has been shown to neutralize enterotoxins of various pathogenic microbes including *Escherichia coli, Vibrio cholerae* and *Salmonella*. See, e.g. U.S. Pat. No. 5,330,975 to Hiroko et al. It has also been shown that α(2-3) sialyllactose (α-Neu5Ac-(2-3)-Gal-β-(1-4)-Glc) interferes with colonization of Helicobacter pylori and thereby prevents or inhibits gastric and duodenal ulcers. See e.g. U.S. Pat. No. 5,514,660 to Zopf et al. Sialyllactose has additionally been proposed to inhibit immune complex formation by disrupting occupancy of the Fc carbohydrate binding site on IgG and to be useful in treating arthritis. See, e.g. U.S. Pat. No. 5,164,374 to Rademacher et al.

To date, commercially available sialyloligosaccharides have been very expensive due to their low quantity in natural sources. For example, α(2-3) sialyllactose and α(2-6) sialyllactose isolated from bovine colostrum, is sold for $75.60 and $83.30 per milligram, respectively (Sigma Chemical Company, 1997).

A focused effort has been directed toward harvesting sialyloligosaccharides from the vast supply of whey made available as a cheese processing waste product. Processes for isolating sialyloligosaccharides have utilized such techniques as ultrafiltration, ion-exchange resins and phase partition chemistry. U.S. Pat. No. 4,001,198 to Thomas and U.S. Pat. No. 4,202,909 to Pederson; U.S. Pat. No. 4,547,386 to Chambers et al.; U.S. Pat. No. 4,617,861 to Armstrong; U.S. Pat. Nos. 4,971,701 and 4,855,056 to Harju et al.; U.S. Pat. No. 4,968,521 to McInychyn; U.S. Pat. No. 4,543,261 to Harmon et al.; U.S. Pat. Nos. 5,118,516 and 5,270,462 to Shimatani; J P Kokai 01-168,693; J P Kokai 03-143,351; J P Kokai 59-184,197; J P Kokoku 40-1234; J P Kokai 63-284,199 and Japanese Patent Publication No. 21234/1965, each of which is herein incorporated by reference in its entirety. Yields of up to 6 grams of α(2-3) sialyllactose sialyloligosaccharide per kilogram of cheese processing waste stream have been reported. U.S. Pat. No. 5,575,916 to Brian et al. which is herein incorporated by reference in its entirety.

2.2. Sialidases and Sialyltransferases

Sialic acids are 9-carbon carboxylated sugars which generally occur as the terminal monosaccharides in oligosaccharide chains. In mammalian cells, sialic acids are most frequently linked to β-galactose with an α(2-3) linkage, and to N-acetylglucosamine and N-acetylgalactosamine with an α(2-6) linkage. Cross et al., 1993, *Annu. Rev. Microbiol.* 47:385–411.

Sialidases catalyze the removal of sialic acid residues from the oligosaccharide chain. Due to the wide variety of substitutions which may occur at various carbons of the sialic acid molecules, there are at least 39 different species of sialic acids. Colli, W., 1993, *FASEB J.* 7:1257–1264. Generally, sialidases exhibit substrate specificity for specific forms of sialic acid linkages. Viral sialidases cleave α(2-3) glycosidic bonds more efficiently than α(2-6) bonds, but bacterial sialidases are not as specific. Cross et al., 1993, *Annu. Rev. Microbiol.* 47:385–411 (citing Corfield et al. 1982, *Sialic Acids: Chemistry, Metabolism and Function*, Vol. 10, New York: Springer-Verlag, pp. 195–261). At low enzyme concentrations, bacterial sialidases exhibit a preference for cleaving α(2-3) or α(2-6) glycosidic bonds. Cross et al., 1993, *Annu. Rev. Microbiol.* 47:385–411.

CMP-sialyltransferases catalyze the transfer of cytidine monophosphate-sialic acid (CMP-sialic acid) residues to acceptor molecules. Although many sialidases exhibit at least some substrate specificity, CMP-sialyltransferases act on specific substrates. Mammalian CMP-sialyltransferases are generally found in the Golgi, however, there is evidence that there may be cell-surface associated CMP-sialyltransferases as well. Cross et al., 1993, *Annu. Rev. Microbiol.* 47:385–411 (citing Roth et al., 1971, *J. Cell Biol.* 51:536–547; Shur, 1991, *Glycobiology* 1:563–575; Yogeeswaran et al., 1974, *Biochem. Biophys. Res. Commun.* 59:591–599).

2.3. *Trypanosoma Cruzi* α(2-3)-Trans-Sialidase

*Trypanosoma cruzi* (Order *Kinetoplastida*) is the intracellular parasite responsible for Chagas diseage, throughout Iberoamerican countries. Chagas disease primarily affects nerve and muscle cells. One serious manifestation of Chagas disease is a chronic progressive fibrotic myocarditis. Colli, 1993, *FASEB J.* 7:1257–1264. Approximately 16–18 million people are infected with *T. cruzi*. Colli, 1993, *FASEB J.* 7:1257–1264.

*T. cruzi* invades a broad range of host cells, and a considerable amount of research has focused on the surface molecules in order to determine which molecules may be involved in parasite/host interaction. Colli, 1993, *FASEB J.* 7:1257–1264. One surface molecule which has generated a great deal of interest is the α(2-3)-trans-sialidase. This molecule has the capability of catalyzing both the removal of sialic acid from a donor saccharide-containing molecule (sialidase activity) and catalyzing the transfer of the sialic acid to an acceptor saccharide-containing molecule (trans-sialidase activity). Schankman et al., 1992, *J. Exp. Med.*

175:567–575. The gene encoding *T. cruzi* trans-sialidase has been cloned and characterized at the molecular level.

The *T. cruzi* α(2-3) trans-sialidase catalyzes the transfer of sialic acid from a donor terminal β-galactosyl sialoglycoconjugate to a terminal β-galactose on an acceptor molequle, Collit W., 1993, *FASEB J.* 7:1257–1264. *T. cruzi* α(2-3) trans-sialidase does not use CMP-sialic acid as a substrate and prefers sialyl α(2-3)-linked to β-galactosyl residues as sialic acid donor molecules over sialyl α(2-6)-, α(2-8)-, and α(2-9)-linked sialic acids. Schenkman et al., 1994, *Annu. Rev. Microbiol.* 48:499–523. Furthermore, *T. cruzi* α(2-3) trans-sialidase cannot use free sialic acid as a substrate. Vandekerckhove et al. 1992, *Glycobiology* 2:541–548. The *T. cruzi* α(2-3) trans-sialidase has a broad pH optimum centered at 7.0. Cross et al., 1993, *Annu Rev. Microbiol.* 47:385–411.

More detailed analysis of the α(2-3) trans-sialidase has revealed that the amino-terminal portion of the protein is responsible for the α(2-3) trans-sialidase activity. Campetella et al., 1994, *Mol. Biochem. Parasitol.* 64:337–340; Schenkman et al., 1994, *J. Biol. Chem.* 269:7970–7975. It has also been determined that there are at least two critical amino acid residues: $Tyr^{342}$ and $Pro^{231}$ of the α(2-3) transsialidase appear to be required for full α(2-3) trans-sialidase activity. Cremona et al., 1995, *Gene* 160:123–25. The importance of $Tyr^{342}$ is demonstrated by the fact that naturally occurring variants of the *T. cruzi* α(2-3) trans-sialidase which have a $Tyr^{342} \rightarrow His$ substitution, lack α(2-3) transsialidase activity. Uemura et al., 1992, *EMBO J.* 11:3837-3844.

Trans-sialidase activity has also been discovered in *Trypanosoma brucei*, the causative agent of African Sleeping Sickness, Endotrypanum spp. and in *Pneumocystis carinii*. Like the *T. cruzi* α(2-3) trans-sialidase, the *T. brucei* transsialidase has a pH optimum of 7.0. However, unlike the *T. cruzi* trans-sialidase, which is expressed during the trypomastigote stage, the *T. brucei* trans-sialidase appears to be expressed only during the procyclic stage of the parasite life cycle, when the parasite resides in the midgut of its insect vector (Glossina spp., the "tsetse fly"). Cross et al., 1993, *Annu Rev. Microbiol.* 47:385–411.

2.4. Sialyllactose Production

A variety of methods for enzymatically producing sialylated oligosaccharides have been described.

U.S. Pat. No. 5,374,541 to Wong et al., describes a method for producing sialyloligosaccharides. According to this method, β-galactosidase is used to form β-galactosyl glycosides in the presence of CMP-sialic acid and α(2-3)- or α(2-6)-CMP-sialyltransferases to form sialylated oligosaccharides. This method does not use α(2-3) trans-sialidase.

U.S. Pat. No. 5,409,817 to Ito et al., discloses a three enzyme process for producing α(2-3) sialylgalactosides. According to this process, CMP-sialyltransferases transfer sialic acid from CMP-sialic acid to acceptor molecules, these acceptor molecules become donor molecules for *Trypanosoma cruzi* α(2-3) trans-sialidase, and CMP-sialic acid is regenerated in the system through the action of CMP-sialic acid synthetase and added free sialic acid.

The process described in U.S. Pat. No. 5,409,817 to Ito et al. specifically requires the addition of free sialic acid. The free sialic acid is converted to CMP-sialic acid by CMP-sialic acid synthetase, and the sialic acid moiety is transferred to an acceptor molecule by CMP-sialyltransferase. According to the disclosure of Ito et al., the formation of these sialylated acceptor molecules is required to drive the α(2-3) trans-sialidase reaction forward.

In addition to free sialic acid, the method of Ito et al., also requires the presence of three enzymes including CMP-sialic acid synthetase and CMP-sialyltransferase. Further, dairy sources and cheese processing waste streams do not contain CMP-sialic acid synthetase.

2.5. Expression of Transgenes in Milk

Numerous foreign proteins have successfully been transgenically expressed in the milk of livestock. Most of this work has focused on the expression of proteins which are foreign to the mammary gland. Colman, A., 1996, *Am. J. Clin. Nutr.* 63:639S–645S. To date, milk specific expression of transgenic livestock has been achieved through operably linking regulatory sequences of milk-specific protein genes to the target protein-encoding gene sequence, microinjecting these genetic constructs into the pronuclei of fertilized embryos, and implanting the embryos into recipient females. See e.g. Wright et al., 1991, *Biotechnology (NY)* 9:830–834; Carver et al., 1993, *Biotechnology (NY)* 11:1263–1270; Paterson et al., 1994, *Appl. Microbiol. Biotechnol.* 40:691–698. Proteins that have been successfully expressed in the milk of transgenic animals, include: α1-antitrypsin (Wright et al., 1991, *Biotechnology (NY)* 9:830–834; Carver et al., 1993, *Biotechnology (NY)* 11:1263–1270); Factor IX (Clark et al., 1989, *Biotechnology (NY)* 7:487–492); protein C (Velander et al., 1992, *Proc. Natl. Acad. Sci. USA*, 89:12003–12007); tissue plasminogen activator (Ebert et al., 1991, *Biotechology (NY)* 9:835–838); and fibrinogen. While most of these transgenes express proteins that supplement the composition of milk, very few, if any of the expressed proteins interact directly with the components of milk to alter the natural milk composition. There is a need for methods providing for the large scale production of α(2-3) sialyloligosaccharides, such as α(2-3) sialyllactose, which have commercial and/or therapeutic valve.

3. SUMMARY OF THE INVENTION

The present invention greatly advances the field of commercial production of sialyloligosaccharides by providing methods for producing sialyloligosaccharides in situ in dairy sources and cheese processing waste streams. The methods of the invention have particular applications in producing α(2-3) sialyllactose in a dairy source prior to, during, or after processing of the dairy source during the cheese manufacturing process, thereby greatly increasing the recoverable yield of α(2-3) sialyllactose from the dairy source.

Dairy sources and cheese processing waste streams are known to contain high concentrations of lactose and numerous α(2-3) sialosides, such as, for example, κ casein, and the gangliosides. Applicants are the first to provide a method for producing α(2-3) sialyllactose in a dairy source or a cheese processing waste stream. More specifically, the method of the present invention uses the catalytic activity of α(2-3) trans-sialidases to exploit the high concentrations of lactose and α(2-3) sialosides which naturally occur in dairy sources, to drive the enzymatic synthesis of α(2-3) sialyllactose. This catalytic activity does not require the presence of CMP-sialic acid synthetase, CMP-sialyltransferase and/or free siallic acid to drive the sialylation of α(2-3) sialyllactose and other α(2-3) sialyloligosaccharides.

Accordingly, the invention provides a novel method for producing α(2-3) sialyloligosaccharides, and specifically, α(2-3) sialyllactose (α-Neu5Ac-(2-3)-Gal-β-(1-4)-Glc), in a dairy source or cheese processing waste stream by catalyzing the sialidation of lactose (Gal-β-(1-4)-Glc). In specific embodiments, the method of the invention is applied to the dairy source prior to or during processing. In another specific embodiment, the method of the present invention is applied after processing of the dairy source (e.g. to a cheese processing waste stream).

The present invention provides a method for producing sialyloligosaccharides in a dairy source. This method comprises contacting a catalytic amount of least one α(2-3) trans-sialidase with a dairy source to form a dairy/trans-sialidase mixture and incubating the dairy/trans-sialidase mixture under conditions suitable for α(2-3) trans-sialidase activity. α(2-3) sialyloligosaccharides produced according to this method are additionally encompassed by the present invention. The invention also provides for recovery of the sialyloligosaccharides contained in the incubated dairy/trans-sialidase mixture or alternatively, in compositions formed after processing of the incubated dairy/trans-sialidase mixture (e.g. a cheese processing waste stream), using techniques which include, but are not limited to, ultrafiltration, diafiltration, nanofiltration, electrodialysis, phase partitioning and ion exchange chromatography.

The present invention also provides a method for producing sialyloligosaccharides in a cheese processing waste stream. This method comprises contacting a catalytic amount of at least one α(2-3) trans-sialidase with a cheese processing waste stream to form a waste stream/trans-sialidase mixture and incubating the waste stream/trans-sialidase mixture under conditions suitable for α(2-3) trans-sialidase activity. α(2-3) sialyloligosaccharides produced according to this method are additionally encompassed by the present invention. The invention also provides for recovery of the sialyloligosaccharides contained in the incubated dairy/trans-sialidase mixture using techniques which include, but are not limited to, ultrafiltration, diafiltration, nanofiltration, electrodialysis, phase partitioning and ion exchange chromatography.

The invention further provides a method for producing α(2-3) sialyllactose. This method comprises contacting a catalytic amount of at least one α(2-3) trans-sialidase with lactose and an α(2-3) sialyloligosaccharide, in the absence of CMP-sialyltransferase, to form a mixture, and incubating this mixture under conditions suitable for α(2-3) trans-sialidase activity. α(2-3) sialyllactose produedd according to this method are additionally encompassed by the present invention. The invention also provides for recovery of the sialyllactose contained in this incubated mixture using techniques which include, but are not limited to, ultrafiltration, diafiltration, nanofiltration, electrodialysis, phase partitioning and ion exchange chromatography.

The invention additionally provides a method of enriching for α(2-3) sialyllactose in milk using transgenic mammals that express an α(2-3) trans-sialidase transgene. According to this method, a transgene comprising an α(2-3) trans-sialidase encoding sequence is operably linked to a regulatory sequence of a gene expressed in mammary tissue and this α(2-3) trans-sialidase/regulatory sequence transgene is then introduced into the germline of a mammal to produce a transgenic mammal. The milk produced by a transgenic mammal demonstrating α(2-3) trans-sialidase activity in mammary tissue, contains enriched α(2-3) sialyllactose concentrations. The invention also provides for recovery of the sialyllactose contained in the milk produced by this transgenic mammal either before or after processing of the milk. Transgenic mammals containing an α(2-3) trans-sialidase encoding sequence operably linked to a regulatory sequence of a gene expressed in mammary tissue are also provided by the invention. Significantly, a dairy source, cheese processing waste stream, and transgenic mammal can be used to produce enriched concentrations of α(2-3) sialyllactose.

As used herein, "trans-sialidase" refers to a compound that catalyzes the transfer of a sialic acid from one saccharide-containing molecule (e.g. oligosaccharide, polysaccharide, glycoprotein or glycolipid) to another saccharide-containing molecule and which does not require the presence of free sialic acid, CMP-sialic acid, synthetase and/or CMP-sialyltransferase in the reaction mixture for its activity.

As used herein, "trans-sialidase activity" refers to the catalytic reaction in which an enzyme catalyzes the removal of a sialic acid from one saccharide-containing molecule and the transfer of the sialic acid to another saccharide-containing molecule, covalently attaching the sialic acid to the acceptor molecule through a glycosidic bond.

As used herein, a "catalytic amount" of α(2-3) trans-sialidase enzyme refers to the quantity of enzyme sufficient to cause the transfer of a sialic acid from one saccharide-containing molecule to another saccharide-containing molecule.

As used herein, "conditions suitable for trans-sialidase activity" encompass appropriate conditions (e.g. temperature, pH and incubation time) sufficient to permit the enzymatic removal of a sialic acid from one saccharide-containing molecule and the transfer of the sialic acid to another saccharide-containing molecule.

As used herein, "α(2-3) sialyloligosaccharides" refer to sugars in which a sialic acid is covalently attached to the 3' carbon of a β-galactose moiety through a glycosidic bond. In the methods of the present invention, α(2-3) sialyloligosaccharides encompass saccharides with any form of sialic acid covalently attached to the 3'-β-galactose.

As used herein, "dairy source" refers to a product of lactation in a mammal, a substance made by the product, or a byproduct thereof. As used herein, "dairy source" includes, but is not limited to, milk, colostrum, a cheese processing mixture, and a composition simulating milk.

As used herein, a "cheese processing mixture" is a compilation of ingredients of dairy processing at any stage during dairy processing (e.g. pasteurization, fermentation, or cheese manufacture) other than the cheese processing waste stream.

As used herein, "a composition simulating milk" is a solution lacking one or more of CMP-sialyltransferase, CMP-synthetase and/or free sialic acid, but which contains at least α(2-3) sialosides to act as donors for the trans-sialidase, lactose and, optionally, appropriate buffering agents to maximize the activity of the α(2-3) trans-sialidase when it is added to the solution.

As used herein, "cheese processing waste stream" refers to a byproduct of cheese manufacture and includes, but is not limited to, whole whey, demineralized whey permeate, the regeneration stream from demineralized whey permeate, whey permeate, crystallized lactose, spray dried lactose, whey powder, edible lactose and lactose. Whey containing sialic acids, is a byproduct obtained when cheese or rennet casein is produced from milks such as cow milk, goat milk, and sheep milk. For example acid whey, is generated by separating the solids when gkim milk is coagulated to form cottage cheese. Acid whey is characterized by a high lactic acid content. When cheese is prepared from whole milk, the remaining liquid is sweet whey which can be further processed by evaporation to form dry whey powder. Sweet whey can also be dried, demineralized and evaporated to form demineralized whey permeate. Sweet whey can also be subjected to ultrafiltration to generate both a whey permeate and a whey protein concentrate. Whey permeate can be further processed by crystallizing lactose to form both lactose and a mother liquor. The mother liquor resulting from crystallizing lactose from a whey permeate is known in the art as "Delac."

The α(2-3) trans-sialidase used according to the method of the present invention encompasses Kinetoplastid trans-sialidases, trans-sialidases derived from Trypanosoma, Endotrypanum, and Pneumocystis, and includes trans-sialidases of *Trypanosoma cruzi, Trypanosoma brucei,* Endotrypanum spp. and *Pneumocystis carinii*. Trans-sialidases that may be used according to the method of the present invention are further defined infra in Section 5.1.

4. BRIEF DESCRIPTION OF THE FIGURES

FIG. 1. Complete nucleotide sequence (SEQ ID NO:1) of *Trypanosoma cruzi* (Genbank D50685) α(2-3) trans-sialidase.

FIG. 2. Deduced amino acid sequence (SEQ ID NO: 2) of *Trypanosoma cruzi* (Genbank D50685) α(2-3) trans-sialidase.

FIG. 3. Nucleotide sequence (SEQ ID NO: 3) of a functional *Trypanosoma cruzi* α(2-3) trans-sialidase lacking the amino acid repeats (Genbank L26499).

FIG. 4. Deduced amino acid sequence (SEQ ID NO: 4) of a functional *Trypanosoma cruzi* α(2-3) trans-sialidase lacking the amino acid repeats (Genbank L26499).

FIG. 5. Effect of pH on α(2-3) sialyllactose enrichment in mozzarella whey. The α(2-3) sialyllactose concentration (μg/mL) is shown as a function of time of incubation of 0.1% α(2-3) trans-sialidase lysate at 25° C. Squares represent pH 4.0; open diamonds represent pH 5.0; circles represent pH 6.0; triangles represent pH 7.0; crossed squares represent pH 8.0; and shaded diamonds represent pH 9.0. α(2-3) sialyllactose enrichment was observed at all pHs tested, with only minimal enrichment observed after 20 minutes at pH 4.0.

Figure 6:
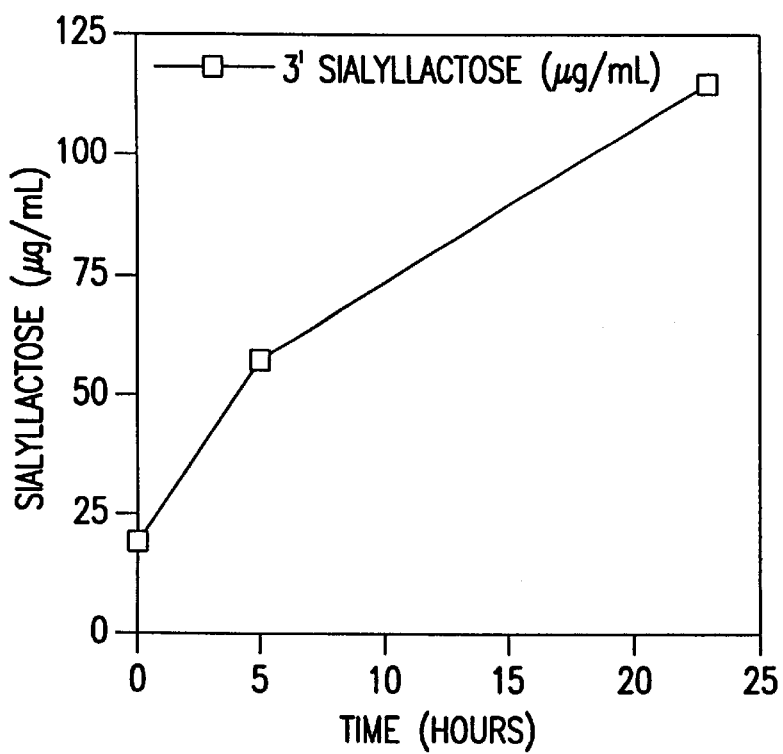

FIG. 6. Enrichment of α(2-3) sialyllactose in skim milk. The concentration of α(2-3) sialyllactose (μg/mL) is shown as a function of time of incubation with 0.1% trans-sialidase lysate at 22° C.

Figure 7A:
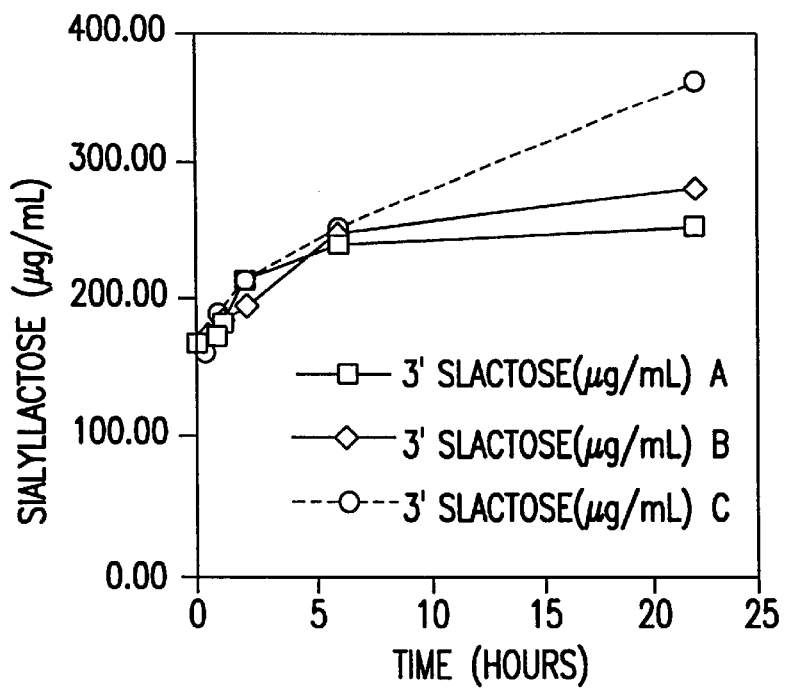
Figure 7B:
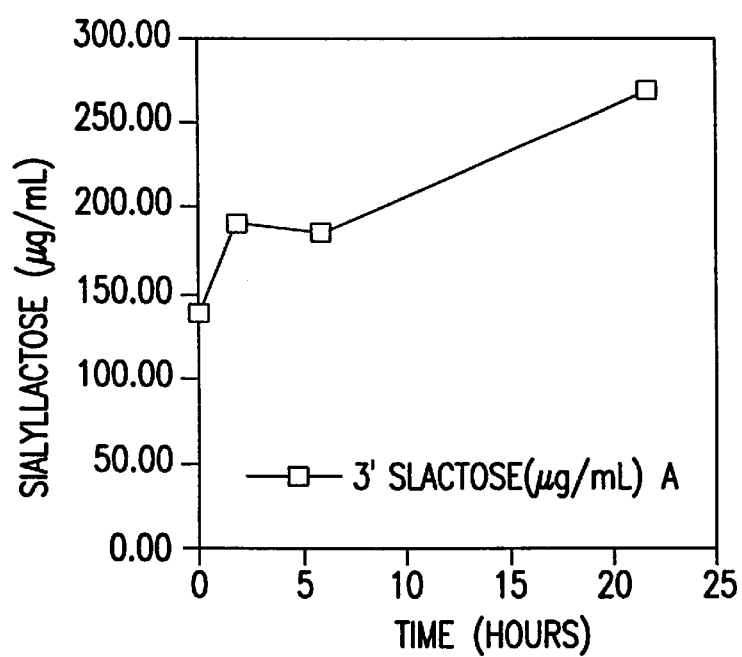

FIGS. 7A–B. Enrichment of α(2-3) sialyllactose in mozzarella whey. The concentration of α(2-3) sialyllactose (μg/mL) is shown as a function of time of incubation of 0.1% α(2-3) trans-sialidase lysate at 25° C. (FIG. 7A) and 23° C. (FIG. 7B).

Figure 8:
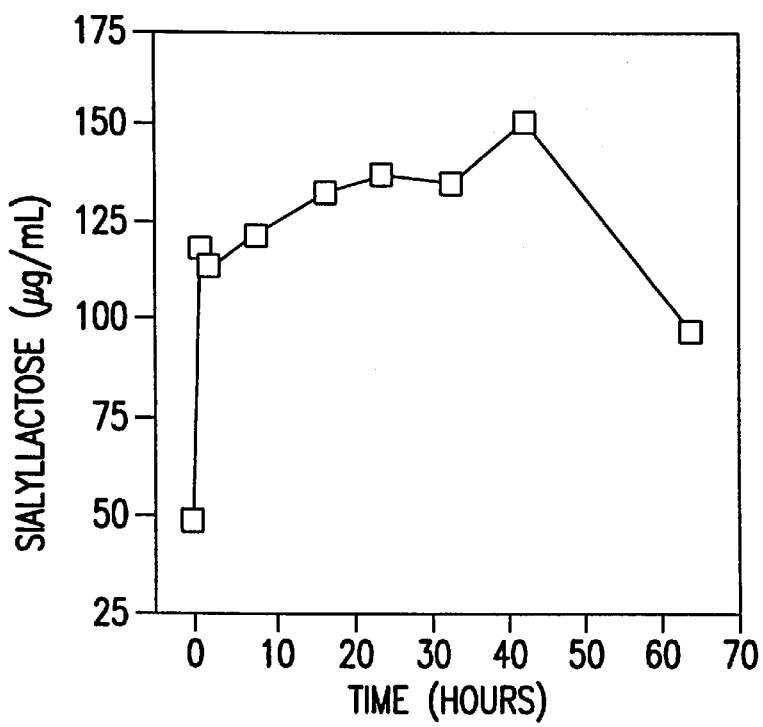

FIG. 8. Enrichment of α(2-3) sialyllactose in Swiss cheese whey. The concentration of α(2-3) sialyllactose (μg/ml) is shown as a function of time of incubation of 0.1% α(2-3) trans-sialidase lysate at 23° C. over 43 hours.

Figure 9:
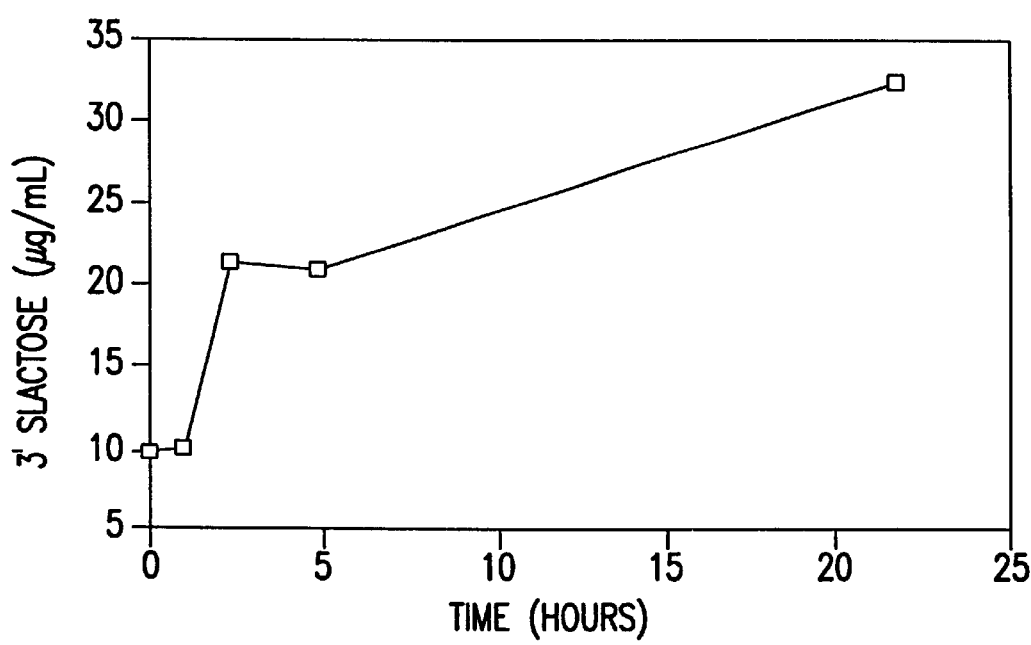

FIG. 9. Enrichment of α(2-3) sialyllactose in a solution containing 20 mg/ml lactose, 5 mg/ml κ-casein at 23° C., over 22 hours.

5. DETAILED DESCRIPTION OF THE INVENTION

The invention relates to methods for producing sialyloligosaccharides in a dairy source, particularly, α(2-3) sialyllactose, by contacting a catalytic amount of α(2-3)-trans-sialidase with a dairy source to form a dairy/trans-sialidase mixture and incubating this mixture under conditions suitable for α(2-3) trans-sialidase activity. The invention also relates to methods for recovering α(2-3) sialylated oligosaccharides from this incubated dairy/trans-sialidase mixture, or alternatively, from compositions formed after processing of the dairy/trans-sialidase mixture (e.g. a cheese processing waste stream). In a specific embodiment, α(2-3) sialyllactose is recovered from the processed composition by ultrafiltration and ion exchange chromatography.

The invention additionally provides for methods of producing α(2-3) sialyloligosaccharides in a cheese processing waste stream by contacting a catalytic amount of trans-sialidase with a cheese processing waste stream to form a waste stream/trans-sialidase mixture and incubating this mixture under conditions suitable for α(2-3) trans-sialidase activity. The invention also relates to methods for recovering α(2-3) sialyloligosaccharides from this incubated waste stream/trans-sialidase mixture.

The methods of the present invention can be used to produce α(2-3) sialyloligosaccharides in any reaction mixture containing α(2-3) sialylated saccharide compositions (e.g. oligosaccharides, polysaccharides, glycoproteins, and glycolipids) and lactose. Starting materials may therefore be derived from all dairy sources (e.g. human and animal milk, whey and colostrum) or alternatively, a mixture of lactose and α(2-3) sialylated saccharide compositions which simulates a dairy source.

5.1. α(2-3) Trans-Sialidase

The α(2-3) trans-sialidase used according to the method of the invention is an α(2-3) trans-sialidase, or derivative (including fragments or fusion proteins), or analog thereof, which is able to catalyze the removal of sialic acid from one saccharide-containing molecule and catalyze the transfer of the sialic acid to a second saccharide-containing moleculoe The α(2-3) trans-sialidases that may be used according to the method of the invention include, but are not limited to, a Kinetoplastid α(2-3) trans-sialidase from a species of the genera Trypanosoma, Endotrypanum, and Pneumocystis, such as, for example, *Trypanosoma cruzi* α(2-3) trans-sialidase, *T. brucei* α(2-3) trans-sialidase (Pontes de Carvalho et al., 1993, *J. Exp. Med.* 177:465–474), *Pneumocystis carinii* trans-sialidase (L. Trimbal, N. Pavia & M. E. A. Pereira, unpublished information as cited in Schenkman et al., 1994, *Annu. Rev. Microbiol.* 48:499–523), and Endotrypanum spp. trans-sialidase (Medina-Acosta et al., 1994, *Mol. Biochem Parasitol.* Nucleic acid sequences of trans-sialidases are known (for example, Genbank Sequence L26499, SPTREMBL:Q26964 (Uemura), SPTREMBL:Q26965 (Uemura), SPTREMBL:Q26966 (Uemura), SPTREMBL:Q26969 (Cremona et al.), Genbank D50685 (Uemura).

In specific embodiments, a polypeptide consisting of or comprising a fragment of at least 50 (continuous) amino acids of an α(2-3) trans-sialidase are used according to the method of the invention. In other embodiments, the fragment consists of at least 100, 150, 200, 250, 300, 350, 400, 450, 500, or 550 amino acids of the α(2-3) trans-sialidase. In further specific embodiments, such fragments are not larger than 500, 400, 300, 200 or 100 amino acids. Derivatives or analogs of a α(2-3) trans-sialidase, include but are not limited to, those molecules that catalyze the transfer of sialic acid from one saccharide-containing molecule (e.g. a oligosaccharide, polysaccharide, glycoprotein, or glycolipid)) to another saccharide-containing molecule and that are encoded by a DNA sequence that hybridizes to the complement of a DNA sequence that encodes a α(2-3) trans-sialidaser such as, for example, those listed above, under high stringency, moderately high stringency, or low stringency conditions.

By way of example and not limitation, procedures using conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10⁶ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which may be used are well known in the art.

By way of example and not limitation, procedures using conditions of high stringency are as follows: prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10⁶ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

By way of example and not limitation, procedures using conditions of moderately high stringency are as follows: filters containing DNA are pretreated for 6 hours to overnight at 55° C. in buffer composed of 6×SSC, 5×Denhart's 0.5% SDS, 100 mg/mL salmon sperm DNA. Hybridizations are carried out in the game solution upon adding 5–20×10⁶ cpm of $^{32}$P-labeled probe and incubated 8–48 hours at 55° C. Washing of filters is done at 60° C. in 1×SSC, 0.1% SDS, with two exchanges after 30 minutes. Other conditions for moderately high stringency screening are known in the art. For further guidance regarding hybridization conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

The invention also relates to α(2-3) trans-sialidase derivatives or analogs made by altering the α(2-3) trans-sialidase sequence by substitutions, additions or deletions that provide for molecules with α(2-3) trans-sialidase activity (i.e., catalyzes the transfer of sialic acid from one saccharide-containing molecule to another). Thus, the α(2-3) trans-sialidase derivatives include polypeptides containing, as a primary amino acid sequence, all or part of the α(2-3) trans-sialidase amino acid sequence including altered sequences in which functionally equivalent amino acid residues are substituted for residues within the sequence resulting in a polypeptide which is functionally active (i.e., a polypeptide possessing trans-sialidase activity). For example, one or more amino acid residues within the sequence can be substituted by another amino acid of a similar polarity which acts as a functional equivalent, resulting in a silent alteration. Conservative substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such α(2-3) trans-sialidase derivatives can be made either by chemical peptide synthesis or by recombinant production from nucleic acid encoding the α(2-3)-trans-sialidase which have been mutated. Any technique for mutagenesis known in the art can be used, including but not limited to, chemical mutagenesis, in vitro site-directed mutagenesis (Hutchinson et al., 1978, J. Biol. Chem 253:6551), use of TAB® linkers (Pharmacia), etc.

The trans-sialidase, or functionally active derivative (including fragments and fusion proteins), or analog used according to the method of the present invention can be obtained by purification from biological tissue or cell culture, or produced by recombinant or synthetic techniques known in the art.

Native α(2-3) trans-sialidase preparations can be obtained from a variety of sources. Standard methods for protein purification may be used to isolate and purify, or partially purify, α(2-3) trans-sialidases from any source known to contain or produce the desired α(2-3) trans-sialidase, e.g., T. cruzi or T. brucai. Such standard protein purification techniques include, but are not limited to, chromatography (e.g., ion exchange, affinity, gel filtration/molecular exclusion chromatography and reversed phase high performance liquid chromatography (RP-HPLC)), centrifugation, differential solubility, and electrophoresis (for a review of protein purification techniques, see, Scopes, Protein Purification; Principles and Procedure, 2nd Ed., C. R. Cantor, Editor, Springer Verlag, New York, N.Y. (1987), and Parvez et al., Progress in HPLC, Vol. 1, Science Press, (1985) Utrecht, The Netherlands). For example, antibodies to trans-sialidases may be generated using techniques known in the art, and can be used to prepare an affinity chromatography column for purifying the respective trans-sialidases by well-known techniques (see, e.g., Hudson & May, 1986, Practical Immunology, Blackwell Scientific Publications, Oxford, United Kingdom).

5.1.1. Recombinant Production of Trans-Sialidase

Recombinant expression techniques can be applied to obtain the α(2-3) trans-sialidases, derivatives, and analogs utilized according to the method of the invention (see, e.g., Sambrook et al., 1989, Molecular Cloning, A Laboratory Manual, Cold Spring Harbor Laboratory, 2d Ed., Cold Spring Harbor, N.Y., Glover, D. M. (ed.), 1985, DNA Cloning: A Practical Approach, MRL Press, Ltd., Oxford, U.K., Vol. I, II). The nucleic acid sequences of α(2-3) trans-sialidases such as, for example, those described above, are known and can be isolated using well-known techniqueg in the art, such as screening a genomic or cDNA library, chemical synthesis, or polymerase chain reaction (PCR). Further, given these known sequences, other α(2-3) trans-sialidases may be cloned using routine recombinant techniques known in the art, such as, for example, PCR and hybridization to the complement of the known nucleic acid sequence under highly stringent, moderately highly stringent, and low stringency conditions, in combination with assays which select for known biochemical properties of the α(2-3) trans-sialidase of interest, or generally, to catalyze the transfer of sialic acid from a donor saccharide-containing molecule to an acceptor saccharide-containing molecule. Cloned α(2-3) trans-sialidase gene sequence can be modified by any of numerous strategies known in the art.

To recombinantly produce a α(2-3) trans-sialidase, derivative or analog, a nucleic acid sequence encoding the α(2-3) trans-sialidase, derivative, or analog, is operatively linked to a promoter such that the α(2-3) trans-sialidase, derivative, or analog is produced from said sequence. For example, a vector can be introduced into a cell, within which cell the vector or a portion thereof is expressed, producing an α(2-3) trans-sialidase or a portion thereof. In a preferred embodiment, the nucleic acid is DNA if the source of RNA polymerase is DNA-directed RNA polymerase, but the nucleic acid may also be RNA if the source of polymerase is RNA-directed RNA polymerase or if reverse transcriptase is present in the cell or provided to produce DNA from the RNA. Such a vector can remain episomal or become chromosomally integrated, as long as it can be transcribed to produce the desired RNA. Such vectors can be constructed by recombinant DNA technology methods standard in the art.

A variety of host-vector systems may be utilized to express the protein-coding sequence. These include, but are not limited to, mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities and depending on the host-vector system utilized, any one of a number of suitable transcription and translation elements may be used.

Expression of an α(2-3) trans-sialidase, derivative, or analog may be controlled by any promoter/enhancer element known in the art. Such promoters include, but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the HSV-1 (herpes simplex virus-1) thymidine kinase promoter (Wagner at al., 1981, Proc. Natl. Acad. Sci. U.S.A. 78:1441–1445), the regulatory sequences of the metallothionein gene (Brinster et al., 1982, Nature 296:19–42); prokaryotic expression vectors such as the β-lactamase promoter (Villa-Kamaroff et al., 1978, Proc. Natl. Acad. Sci. U.S.A. 75:3727–3731), or the tac promoter (DeBoer et al., 1983, Proc. Natl. Acad. Sci. U.S.A. 80:21–25); see also "Useful Proteins from Recombinant Bacteria" in Scientific American, 1980, 242:74–94; plant expression vectors comprising the nopaline synthetase promoter region (Herrera-Estrella et al., 1983, Nature 303:209–213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in traneggnic animals; elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5;1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 49:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378). The promoter element which is operatively linked to the nucleic acid encoding trans-sialidase, derivative or analog, can also be a bacteriophage promoter with the source of the bacteriophage RNA polymerase expressed from a gene for the RNA polymerase on a separate plasmid, e.g., under the control of an inducible promoter, for example, the nucleic acid encoding trans-sialidase, derivative, or analog, operatively linked to the T7 RNA polymerase promoter with a separate plasmid encoding the T7 RNA polymerase. In a preferred embodiment of the invention, expression of a α(2-3) trans-sialidase, derivative, or analog is controlled by a regulatory sequence of a gene expressed in mammary tissue, such as, for example, the regulatory sequence of a gene encoding a milk specific protein (see e.g., Wright et al., 1991, Biotechnology (NY) 9:830–834; Carver et al., 1993, Biotechnology (NY) 11:1263–1270); Clark et al., 1989, Biotechnology (NY) 7:487–492; Velander et al., 1992, Proc. Natl. Acad. Sci. USA, 89:12003–12007; Ebert et al., 1991, Biotechology (NY) 9:835–838).

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered α(2-3) trans-sialidase, derivative or analog may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

The α(2-3) trans-sialidase-encoding nucleic acid sequence can be mutated in vitro or in vivo, to create and/or destroy translation, initiation, and/or termination sequences, or to create variations in coding regions. Any technique for mutagenesis known in the art can be used, including but not limited to, in vitro site-directed mutagenesis (Hutchinson et al., 1978, J. Biol. Chem. 253:6551), use of TAB® linkers (Pharmacia), etc.

The experimentation involved in mutagenesis consists primarily of site-directed mutagenesis followed by phenotypic testing of the altered gene product. Some of the more commonly employed site-directed mutagenesis protocols take advantage of vectors that can provide single stranded as well as double stranded DNA, as needed. Generally, the mutagenesis protocol with such vectors is as follows. A mutagenic primer, i.e., a primer complementary to the sequence to be changed, but consisting of one or a small number of altered, added, or deleted bases, is synthesized. The primer is extended in vitro by a DNA polymerase and, after some additional manipulations, the now double-stranded DNA is transfected into bacterial cells. Next, by a variety of methods, the desired mutated DNA is identified, and the desired protein is purified from clones containing the mutated sequence. For longer sequences, additional cloning steps are often required because long inserts (longer than 2 kilobases) are unstable in those vectors. Protocols are known to one skilled in the art and kits for site-directed mutagenesis are widely available from biotechnology supply companies, for example from Amersham Life Science, Inc. (Arlington Heights, Ill.) and Stratagene Cloning Systems (La Jolla, Calif.).

In specific embodiments, the α(2-3) trans-sialidase derivative or analog used according to the method of the invention is generated by site-directed mutagenesis of the DNA encoding a non-functional α(2-3) trans-sialidase. In a specific embodiment the codon encoding for the amino acid at position 342 (relative to $Try^{342}$ of Genbank L26499) is mutated to encode for a tyrosine residue. In the another specific embodiment, a more active α(2-3) trans-sialidase is generated, by the site-directed mutagenesis of DNA encoding a less active α(2-3) trans-sialidase by mutating the codon encoding as for the amino acid at position 231 of the less active α(2-3) trans-sialidase (relative to $Pro^{231}$ of Genbank L26499) to encode a proline residue.

In other specific embodiments, the α(2-3) trans-sialidase derivative or analog may be expressed as a fusion, or chimeric protein product (comprising the protein, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art (see e.g., Section 5.6).

5.1.2. Chemical Synthesis of Trans-Sialidase

In addition, α(2-3) trans-sialidases, derivatives (including fragments and chimeric proteins), and analogs can be chemically synthesized. See, e.g., Clark-Lewis et al., 1991, Biochem. 30:3128–3135 and Merrifield, 1963, J. Amer. Chem. Soc. 85:2149–2156. For example, α(2-3) trans-sialidases, derivatives and analogs can be synthesized by solid phase techniques, cleaved from the resin, and purified by preparative high performance liquid chromatography (e.g., see Creighton, 1983, Proteins, Structures and Molecular Principles, W. H. Freeman and Co., N.Y., pp. 50–60). α(2-3) trans-sialidases, and derivatives and analogs thereof can also be synthesized by use of a peptide synthesizer. The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34–49). Furthermore, if desired, nonclassical amino acids or chemical amino acid analogs can be introduced as a substitution or addition into the α(2-3) trans-sialidase, derivative or analog. Non-classical amino acids include but are not limited to the D-isomers of the common amino acids, 2,4-diaminobutyric acid, α-amino isobutyric acid, 4-aminobutyric acid, Abu, 2-amino butyric acid, γ-Abu, ϵ-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, degigner amino acids such as β-methyl amino acids, Cα-methyl amino acids, Nα-methyl amino acids, and amino acid analogs in general. Furthermore, the amino acid can be D (dextrorotary) or L (levorotary).

By way of example, but not by way of limitation, proteins (including peptides) of the invention can be chemically synthesized and purified as follows: α(2-3) trans-sialidases, derivatives and analogs can be synthesized, by employing the N-α-9-fluorenylmethyloxycarbonyl or Fmoc solid phase peptide synthesis chemistry using a Rainin symphony Multiplex Peptide Synthesizer. The standard cycle used for coupling of an amino acid to the peptide-resin growing chain generally includes: (1) washing the peptide-resin three times for 30 seconds with N,N-dimethylformamide (DMF); (2) removing the Fmoc protective group on the amino terminus by deprotection with 20% piperdine in DMF by two washes for 15 minutes each, during which process mixing is effected by bubbling nitrogen through the reaction vessel for one second every 10 seconds to prevent peptide-resin settling; (3) washing the peptide-resin three times for 30 seconds with DMF; (4) coupling the amino acid to the peptide resin by addition of equal volumes of a 250 mM solution of the Fmoc derivative of the appropriate amino acid and an activator mix consisting or 400 mM N-methylmorpholine and 250 mM (2-(1H-benzotriazol-1-4))-1,1,3,3-tetramethyluronium hexafluorophosphate (HBTU) in DMF; (5) allowing the solution to mix for 45 minutes; and (6) washing the peptide-resin three times for 30 seconds of DMF. This cycle can be repeated as necessary with the appropriate amino acids in sequence to produce the desired polypeptide. Exceptions to this cycle program are amino acid couplings predicted to be difficult by nature of their hydrophobicity or predicted inclusion within a helical formation during synthesis. For these situations, the above cycle can be modified by repeating step 4 a second time immediately upon completion of the first 45 minute coupling step to "double couple" the amino acid of interest. Additionally, in the first coupling step in polypeptide synthesis, the resin can be allowed to swell for more efficient coupling by increasing the time of mixing in the initial DMF washes to three 15 minute washes rather than three 30 second washes. After polypeptide synthesis, the peptide can be cleaved from the resin as follows: (1) washing the polypeptide-resin three times for seconds with DMF; (2) removing the Fmoc protective group on the amino terminus by washing two times for 15 minutes in 20% piperdine in DMF; (3) washing the polypeptide-resin three times for 30 seconds with DMF; and (4) mixing a cleavage cocktail consisting of 95% trifluoroacetic acid (TFA), 2.4% water, 2.4% phenol, and 0.2% triisopropysilane with the polypeptide-resin for two hours, then filtering the peptide in the cleavage cocktail away from the resin, and precipitating the peptide out of solution by addition of two volumes of ethyl ether. To isolate the polypeptide, the ether-peptide solution can be allowed to sit at −20° C. for 20 minutes, then centrifuged at 6,000×G for 5 minutes to pellet the polypeptide, and the polypeptide can be washed three times with ethyl ether to remove residual cleavage cocktail ingredients. The final polypeptide product can be purified by reversed phase high pressure liquid chromatography (RP-HPLC) with the primary solvent consisting of 0.1% TFA and the eluting buffer consisting of 80% acetonitrile and 0.1% TFA. The purified polypeptide can then be lyophilized to a powder.

5.2. Assays for α(2-3) Trans-sialidase Activity

The invention is based in part on the discovery that the addition of α(2-3) trans-sialidase to a dairy source in sufficient quantities to catalyze the transfer of sialic acids from the sialyloligosaccharide population of the dairy source will favor the sialylation of lactose due to the high concentration of lactose in dairy sources. Thus, the ability of α(2-3) trans-sialidases, and derivatives and analogs thereof to catalyze the transfer of sialic acid from an α(2-3) sialyloligosaccharide donor source to an oligosaccharide acceptor having a β-galactose moiety at its non-reducing terminus is indicative of the usefulness of these proteins, derivatives, and analogs in producing sialyloligosaccharides in a dairy source or cheese processing waste stream according to the methods of the present invention.

The trans-sialidases that may be used according to the methods of the invention encompass all protein sequences with functional α(2-3) trans-sialidase activity. The α(2-3) trans-sialidases, therefore, are defined by catalytic activity in which the α(2-3) trans-sialidase directs the transfer of a sialic acid from one saccharide containing molecule (e.g., oligosaccharide, polysaccharide, glycoprotein, or glycolipid) to another. Assays for α(2-3) trans-sialidase activity are well known in the art and may be applied according to the present invention, both to identify α(2-1) trang-gialidases, derivatives and analogs demonstrating the requisite catalytic activity, and also for optimization of reaction parameters (e.g. concentration, temperature, pH and incubation time) for incubating the α(2-3) trans-sialidase, derivative, or analog with the dairy source or cheese processing waste stream.

In one embodiment, α(2-3) trans-sialidase activity is measured using the method described in Vandekerckhove, et al. 1992, Glycobiology 2:541–548. Briefly, α(2-3) trans-sialidase is incubated in 20 mM Hepes buffer (Sigma H-3375) at pH=7.2 in the presence of α(2-3) sialyllactose and [D-glucose-1-$^{14}$C]lactose (60 mCi/mmol) (Amersham, Arlington Heights, Ill.). Reactions are stopped by the addition of 20 μl ethanol. The resulting compounds are analyzed by thin layer chromatography (TLC) on silica gel plates (EM Science, HPTLC Fertigplatten Kieselgel 60F254, 10×10 cm) and chromatographed in ethanol-n-butanol-pyridine-water-acetic acid [100:1010:30:3 (v/v)]. Sialic acid-containing molecules are visualized by resorcinol staining against Neu5Ac, MU-Neu5Ac, α(2-3) sialyllactose and α(2-6) sialyllactose standards.

Other assays for α(2-3) trans-sialidase activity are known in the art and may be used according to the present invention to assess for and/or to optimize α(2-3) trans-sialidase activity. Further, assays for glycosyltransferase activity known in the art may also be routinely modified so as to test for and/or optimize α(2-3) trans-sialidase activity.

5.3. Enrichment of α(2-3) Sialyloligosaccharides Including α (2-3) Sialyllactose The invention provides methods for producing sialyloligosaccharides, particularly α(2-3) sialyllactose, in a dairy source or in a cheese processing waste stream.

In one embodiment, the present invention provides a method for producing sialyloligosaccharides in a dairy source. This method comprises contacting a catalytic amount of at least one α(2-3) trans-sialidase with a dairy source to form a dairy/trans-sialidase mixture, and incubating the dairy/trans-sialidase mixture under conditions suitable for α(2-3) trans-sialidase activity.

In another embodiment, the present invention provides a method for producing sialyloligosaccharides in a cheese processing waste stream. This method comprises contacting a catalytic amount of at least one α(2-3) trans-sialidase with a cheese processing waste stream to form a waste stream/trans-sialidase mixture and incubating the waste stream/trans-sialidase mixture under conditions suitable for α(2-3) trans-sialidase activity.

In an additional embodiment of the present invention, sialyloligosaccharides are produced and recovered from a dairy source by a method comprising contacting a catalytic amount of at least one α(2-3) trans-sialidase with a dairy source to form a dairy/trans-sialidase mixture, incubating the dairy/trans-sialidase mixture under conditions suitable for α(2-3) trans-sialidase activity, and recovering the sialyloligosaccharides from the incubated dairy/trans-sialidase mixture.

The present invention also provides a method for producing sialyloligosaccharides in a dairy source which is subsequently processed for cheese manufacture, followed by recovery of the sialyloligosaccharides from the cheese processing waste stream. When sialyloligosaccharides are produced in a dairy source, processed for cheese manufacture and recovered from the cheese processing waste stream by the method of the present invention, the method comprises contacting a catalytic amount of at least one α(2-3) trans-sialidase with a dairy source to form a dairy/trans-sialidase mixture, incubating the dairy/trans-sialidase mixture under conditions suitable for α(2-3) trans-sialidase activity, processing the incubated dairy/trans-sialidase mixture using any known protocol for the manufacture of cheeses, and recovering the sialyloligosaccharides from the cheese processing waste stream derived from the incubated dairy/trans-sialidase mixture.

In another embodiment of the present invention, sialyloligosaccharides are produced in and recovered from cheese processing waste streams by a method comprising contacting a catalytic amount of at least one α(2-3) trans-sialidase with a cheese processing waste stream to form a waste stream/trans-sialidase mixture, incubating the waste stream/trans-sialidase mixture under conditions suitable for α(2-3) trans-sialidase activity, and recovering sialyloligosaccharides from the incubated waste stream/trans-sialidase mixture.

In each embodiment of the methods of the present invention, the α(2-3) trans-sialidases encompass molecules with enzymatic activity wherein a sialic acid is transferred from one saccharide-containing molecule to another saccharide-containing molecule. The saccharide-containing molecules may be oligosaccharides, polysaccharides, glycoproteins or glycolipids. The α(2-3) trans-sialidases used according to the methods of the present invention are further defined supra in Sections 3.1 and 5.1.

The α(2-3) trans-sialidase used according to the methods of the present invention may be a purified α(2-3) trans-sialidase, derivate or analog; a partially purified α(2-3) trans-sialidase, derivative or analog; or a crude or filtered eukarytic or bacterial (e.g. *E. coli*) lysate containing α(2-3) trans-sialidase activity. Optimal enzyme concentrations used according to the methods of the present invention may beg routinely determined using techniques known in the art. In specific embodiments, the concentration of α(2-3) trans-sialidase used according to the methods of the invention is at least 0.001, 0.005, 0.01, 0.05, 0.075, 0.10 or 0.4 units/ml (wherein one unit is defined as the concentration of enzyme required to produce 1 μmol NAN-α(2-3)-Gal-β(1-4)-GlcNAc-β(1-3)-Gal-β(1-4)-Glc (LST-d)/min in a standard assay using α(2-3)-sialyllactose and Gal-β(1-4)-GlcNAc-β(1-3)-Gal-β(1-4)-Glc (lacto-N-neotetraose, LNnT) as substrates).

The dairy sources used in the methods according to the present invention include, but are not limited to, milk, colostrum, a cheese processing mixture, or a composition simulating milk. As used herein, the phrase cheese processing mixture refers to a compilation of ingredients of dairy processing at any stage during dairy processing (e.g., cheese manufacture) other than the cheese processing waste stream. A composition simulating milk is a solution lacking one or more of CMP-sialyltransferase, CMp-gynthetase and/or free sialic acid, but which contains at least $\alpha$(2-3) sialosides to act as donors for the $\alpha$(2-3) trans-sialidase, lactose and, optionally, appropriate buffering agents to maximize the activity of the $\alpha$(2-3) trans-sialidase when it is added to the solution. Alternatively, a composition simulating milk is a solution containing at least $\alpha$(2-3) sialosides to act as donors for the $\alpha$(2-3) trans-sialidase and lactose, and wherein the presence of free sialic acid, CMP-sialytransferase and/or CMP-synthetase is not required to drive the sialylation of lactose by $\alpha$(2-3) trans-sialidase. A cheese processing waste stream is the portion of cheese manufacturing not retained for cheese after formation of curd. The cheese processing waste stream typically refers to the fluid drained from curd, which is frequently discarded. A cheese processing waste stream of the present invention includes, but is not limited, to whole whey, demineralized whey permeate, the regeneration stream from demineralized whey permeate, whey permeate, crystallized lactose, spray dried lactose, whey powder, edible lactose, and lactose.

In each embodiment of the present invention, the $\alpha$(2-3) trans-sialidase is contacted with the dairy source or cheese processing waste stream and the resulting mixture may be agitated, stirred, mixed, or subjected to any other method of combining. Whether the $\alpha$(2-3) trans-sialidase is added to colostrum, milk, a cheese processing mixture, a composition simulating milk, or to milk that has undergone some processing, may dictate the amount of stirring or mixing which may be required. While milk is relatively fluid, processed milk, such as milk being processed for cheese, may become quite viscous and require more agitation, stirring, mixing, or the like for efficient enzymatic activity to occur. Likewise, a cheese processing waste stream may be a viscous solution and require similar forms of agitation, stirring, mixing, and the like, for efficient enzymatic activity.

Conditions suitable for producing sialyloligosaccharides, particularly $\alpha$(2-3) sialyllactose, in a dairy source or cheese processing waste stream by the methods of the present invention, may be determined and optimized by routine techniques known in the art. In one embodiment, the dairy source or cheese processing waste stream is initially chilled to 2–20° C.

The optimal time to incubate the dairy/trans-sialidase mixture generated according to the present invention may be routinely determined by techniques known in the art. In specific embodiments, the dairy/trans-sialidase mixture is incubated for a period of at least 0.5, 1.0, 5.0 or 10.0 hours. In a preferred embodiment, the dairy/trans-sialidase mixture is incubated for 12–30 hours. In a more preferred embodiment, the dairy/trans-sialidase mixture is incubated for 20–25 hours.

The optimal temperature to incubate the dairy/trans-sialidase mixture generated according to the methods of the present invention may be routinely determined by techniques known in the art. In specific embodiments, the dairy/trans-sialidase mixture is incubated at about 0–30° C. or 2–20° C. In preferred embodiments the dairy/trans-sialidase mixture is incubated at 5–15° C. or 8–12° C. In embodiments where the dairy source is a composition simulating milk, the dairy/trans-sialidase mixture may be incubated at about 0–45° C., 10–45° C., or 20–40° C.

The optimal pH to incubate the dairy/trans-sialidase mixture according to the present invention may be routinely determined by techniques known in the art. In specific embodiments, the dairy/trans-sialidase mixture is incubated at a pH of about pH 5–9, more preferably at about pH 6–8, and most preferably the pH is at about 7.

Further conditions to optimize the incubation of the dairy/trans-sialidase mixture will be apparent to those skilled in the art and are within the scope of the present invention. In a specific embodiment, the dairy/trans-sialidase mixture may be agitated, stirred, shaken, mixed, or the like, to assist the even distribution of enzyme within the mixture.

In one embodiment of the invention, exogenous $\alpha$(2-3) sialyloligosaccharides are added to the dairy/trans-sialidase mixture. The supplemented exogenous $\alpha$(2-3) sialyloligosaccharides may contain a single homogeneous $\alpha$(2-3) sialyloligosaccharide population, or alternatively, may consist of a mixture of different $\alpha$(2-3) sialyloligosaccharides. $\alpha$(2-3) sialyloligosaccharide supplemented during this incubation step should be selected so as to minimize possible negative effects upon the taste, texture, appearance or quality of the dairy product (e.g., cheese).

Following incubation, the milk may be pasteurized by any method of pasteurization known in the art, including, but not limited to, HTST (High Temperature, Short Time Sterilizer/Pasteurizer) at 161°F. for 18 seconds and cooled to 80° F. Sialyloligosaccharides, including, but not limited to, $\alpha$(2-3) sialyllactose, may be recovered from the incubated dairy/trans-sialidase mixture or from the pasteurized dairy/trans-sialidase mixture by the methods described infra in Section 5.4. Where the dairy/trans-sialidase mixture is to be used to manufacture cheese, the dairy/trans-sialidase mixture is collected and processed for making cheese. Alternatively, milk may be pasteurized batchwise (rise and drop of a whole batch to 160°F. is one protocol used) or by HTST pasteurizer/heat exchanger (quick rise to 160° F., hold for 2 minutes, quick chill to 80° F.). Milk may also be sterilized by UHT (ultrahigh temperature sterilization) (quick rise to 270° F., hold for 6 seconds, quick chill to 80° F.). Depending on the subsequent process, this method of sterilization may use heat exchange or clean steam injection. In an alternative embodiment of the invention, the dairy source is processed for cheese manufacture and the sialyloligosaccharides are recovered from the cheese processing waste stream by the methods described infra in Section 5.5.

In another embodiment of the invention, at least one $\alpha$(2-3) trans-sialidase is contacted with a cheese processing waste stream.

The optimal time to incubate the waste stream/trans-sialidase mixture according to this embodiment may be routinely determined by techniques known in the art. In specific embodiments, the waste stream/trans-sialidase mixture is incubated for a period of at least 0.5, 1.0, 5.0 or 10.0 hours. In a preferred embodiment, the waste stream/trans-sialidase mixture is incubated for 5–45 hours. In a more preferred embodiment, the waste stream/trans-sialidase mixture is incubated for 10–35 hours.

The optimal temperature to incubate the waste stream/trans-sialidase mixture according to the present invention may be routinely determined by techniques known in the art. In specific embodiments, the waste stream/trans-sialidase mixture is incubated at about at 2–40° C., preferably 15–37° C., most preferably 22–27° C.

The optimal pH to incubate the dairy source/trans-sialidase mixture according to the present invention may be routinely determined by techniques known in the art. In specific embodiments, the waste stream/trans-sialidase mixture is incubated at a pH of about 4–9, more preferably at about pH 6–8, and most preferably the pH is at about pH 7.

Further conditions to optimize the incubation of the waste stream/trans-sialidase mixture will be apparent to those skilled in the art and are within the scope of the present invention. In specific embodiments the waste stream/trans-sialidase mixture may be agitated, stirred, shaken, mixed, or the like, to assist the even distribution of enzyme within the mixture.

In one embodiment of the invention, exogenous $\alpha(2\text{-}3)$ sialyloligosaccharides are added to dairy source/trans-sialidase mixture. The supplemented exogenous $\alpha(2\text{-}3)$ sialyloligosaccharides may contain a single homogeneous $\alpha(2\text{-}3)$ sialyloligosaccharide population, or alternatively, may consist of a mixture of different $\alpha(2\text{-}3)$ sialyloligosaccharides.

Following incubation of the waste stream/trans-sialidase mixture, sialyloligosaccharides, including, but not limited to $\alpha(2\text{-}3)$sialyllactose may be recovered from the incubated waste stream/trans-sialidase mixture by the methods described infra in Section 5.4.

5.4. Recovery of Sialyloligosaccharides

Sialyloligosaccharides produced according to the methods of the present invention may be recovered from the dairy source before or during processing (e.g., pasteurization, fermentation, and/or one or more of the other processing steps involved in the manufacture of cheese or another dairy product). Alternatively, sialyloligosaccharides produced according to the methods of the present invention may be recovered after processing of the dairy source (e.g. from a cheese processing waste stream). The sialyloligosaccharides produced according to the methods of the invention may be recovered using methods known in the art, including, but not limited to, ultrafiltration, difiltration, electrodialysis, ion exchange chromatography and phase partition chemistry.

In specific embodiments of the invention, $\alpha(2\text{-}3)$ sialyloligosaccharides produced according to the methods of the invention, are recovered from a cheese processing waste stream (i.e., any waste stream or byproduct generated during cheese making process). Whey containing sialic acids, is a byproduct obtained when cheese or rennet casein is produced from milks such as cow milk, goat milk, and sheep milk. For example acid whey, is generated by separating the solids when skim milk is coagulated to form cottage cheese. Acid whey is characterized by a high lactic acid content. When cheese is prepared from whole milk, the remaining liquid is sweet whey, which can be further processed by evaporation to form dry whey powder. Sweet whey can also be dried, demineralized and evaporated to form demineralized whey permeate. Sweet whey can also be subjected to ultrafiltration to generate both a whey permeate and a whey protein concentrate. Whey permeate can be further processed by crystallizing lactose to form both lactose and a mother liquor. The mother liquor resulting from crystallizing lactose from a whey permeate is known in the art as "Delac."

When $\alpha(2\text{-}3)$ trans-sialidase is contacted with a dairy source before or during cheese manufacture and sialyloligosaccharides are recovered from a cheese processing waste stream, suitable cheese processing waste streams include but are not limited to, whole whey, demineralized whey permeate, the regeneration stream from demineralized whey permeate, whey permeate, crystallized lactose, spray dried lactose, whey powder, edible lactose and lactose. Preferably the aqueous mother liquor material resulting from crystallizing lactose (i.e., Delac) is used. When $\alpha(2\text{-}3)$ trans-sialidase is contacted with a cheese processing waste stream and sialyloligosaccharides are thereafter recovered, suitable cheese processing waste streams include colostrum, milk, milk powder, whole whey, demineralized whey permeate, the regeneration stream from demineralized whey permeate, whey permeate, and whey powder.

Fluid cheese whey is typically dried so as to produce a non-hygroscopic, highly dispersable powder. Fresh fluid whey is clarified by passing through a desludging type clarifier. The whey is separated to remove fat, then concentrated in double or triple effect evaporators to a solids content of about 62% by weight. The solids can be removed by separation at room temperature, or more preferably, the concentrated whey is cooled before the solids are removed.

When the cheese processing waste stream to be processed is the solids obtained from drying whey, the solids can be first dissolved in water, preferably in an amount of about 1 to 620 g, preferably 50 to 200 g, more preferably about 100 g of solids per Liter of water. Dissolution of the solids obtained from drying cheese whey can be conducted at room temperature or at elevated temperatures to accelerate the dissolution process and increase the amount of dissolved solids. Preferably, temperatures of from 20–80° C. are suitable. Alternatively, the solids can be processed directly by extraction with a solvent.

In one embodiment of the invention, sialyloligosaccharides produced according to the methods of the invention are recovered from a dairy source or cheese processing waste stream by a method comprising: adjusting the pH of the dairy source or cheese processing waste stream to form an acidic mixture; contacting this acidic mixture with a cation exchanger; and concentrating and desalting the eluent. See e.g., Shimatani et al., U.S. Pat. No. 5,270,462, the contents of which are herein incorporated by reference herein in its entirety).

In another embodiment of the invention, sialyloligosaccharides produced according to the methods of the invention are recovered from a dairy source or cheese processing waste stream by a method comprising: subjecting a dairy source or cheese processing waste stream to ultrafiltration, fractionating at 20,000 to 500,000 Daltons at a pH of 4.0 to 6.0 to form a ultrafiltrate and subjecting the resulting ultrafiltrate to a second ultrafiltration, fractionating at 1,000 to 10,000 Daltons at a pH of 6.0 to 8.0 under 0.2 to 2.0 MPa, to remove impurities such as protein. See e.g., JP Kokai 01-168,693, the contents of which are incorporated by reference in its entirety.

In another embodiment of the invention, sialyloligosaccharides produced according to the methods of the invention are recovered from a dairy source or cheese processing waste stream by a method comprising: desalting the dairy source or cheese processing waste stream and passing the desalted solution through an anion exchange column. See e.g., JP Kokai 59-184,197 the contents of which are herein incorporated by reference in its entirety.

Other methods which may be used during the recovery of sialyloligosaccharides produced according to the methods of the present invention include ultrafiltration (see e.g., U.S. Pat. No. 4,001,198 to Thomas and U.S. Pat. No. 4,202,909 to Pederson); concentration and addition of a divalent cation (see e.g., U.S. Pat. No. 4,547,386 to Chambers et al.); separation and fermentation (see e.g., U.S. Pat. No. 4,617, 861 to Armstrong); demineralization using an electrolytic cell (see e.g., U.S. Pat. Nos. 4,971,701 and 4,855,056 to Harju et al.); separation on a bed of strongly acidic cation exchange resin (see e.g., U.S. Pat. No. 4,543,261 to Harmon et al.); electrodialysis or an ion exchange by a cation-exchange resin and a strongly basic anion-exchange resin, or electrodialysis and ion exchange by the cation-exchange resin and the strongly basic anionexchange resin to desalt the permeate (see e.g., U.S. Pat. No. 5,118,516 to Shimatani). The disclosures of each of the references cited in this paragraph are incorporated by reference in their entireties.

In a preferred embodiment, the sialyloligosaccharides produced according to the methods of the invention are recovered from a dairy source or cheese processing waste stream utilizing an anion exchange resin. According to this embodiment, the dairy source or cheese processing waste stream is optionally pretreated to remove positively charged materials using techniques known in the art (see e.g., DeWitt et al., 1986, Neth. Milk Dairy J. 40:41–56; and Ayers et al., 1986, New Zealand J. Dairy Sci. & Tech. 21:21–35; JP Kokai 52-151200 and 63-39545 and JP 2-104246 and 2-138295).

Suitable cation exchange resins may be prepared by conventional techniques known to those of ordinary skill in the art. For example, a suitable cation exchange resin may be produced from a mixture of polymerizable monofunctional and polyfunctional monomer by radical emulsion polymerization techniques, then functionalized with acidic groups such as carboxylic acid groups or sulfonic acid groups that exist in the protonated form.

The degree of crosslinking in the cation exchange resin can be chosen, depending on the operating conditions of the cation exchange column. A highly crosslinked resin offers the advantage of durability and a high degree of mechanical integrity, however suffers from a decreased porosity and a drop off in mass-transfer. A low-crosslinked resin is more fragile and tends to swell by absorption of mobile phase. A suitable resin may have from 2 to 12% crosslinking, preferably 8% crosslinking.

The particle size of the cation exchange resin is selected to allow for efficient flow of the dairy source or cheese processing waste stream, while still effectively removing the positively charged materials, A suitable particle size for a column 30×18 cm is 100–200 mesh.

Suitable cation exchange resins include but are not limited to CM-Sephadex, SP-Sephadex, CM-Sepharose, S-Sepharose, CM-Cellulose, Cellulose Phosphate, Sulfoxyethyl-Cellulose, Amberlite, Dowex-50W, Dowex HCR-S, Dowex Macroporous Resin, Duolit C433, SP Trisacryl Plus-M, SP Trisacryl Plus-LS, Oxycellulose, AG 50W-X2, AG50W-X4, AG50W-X8, AG 50W-X12, AG 50W-X16, AG MP-50 Resin, Bio-Rex 70. More preferably suitable resins are DOWEX TM 50 x 8 (an aromatic sulfonic acid linked to a polystyrene crosslinked resin from Dow Chemical) and AMBERLYST TM-15, AMBERLITE TM IR-120 AND AMBERLITE TM-200 acidic resins.

The dairy source or cheese processing waste stream can be contacted with the cation exchange resin, in any suitable manner which would allow positively charged materials to be absorbed onto the cation exchange resin. Preferably, the cation exchange resin is loaded onto a column, and the dairy source or cheese processing waste stream is passed through the column, to remove the positively charged materials. An amount of cation exchange resin is selected to affect removal of the positively charged materials, and will vary greatly depending on the dairy source or cheese processing waste stream being treated. Typically, if a whey permeate is being treated, the loading ratio of cheese processing waste stream to cation exchange resin may be from 5 to 20, preferably from 8–15, more preferably from 9 to 12:1 v/v.

When contacting is effected in a column, the dairy source or cheese processing waste stream is preferably passed at a rate of from 1 to 70 cm/min, preferably from 2 to 15 cm/min, more preferably at a rate of 4.6 cm/min. A suitable pressure may be selected to obtain the desired flow rate. Typically a pressure of from 0 to 100 PSIG is selected. Suitable flow rates may also be obtained by applying a negative pressure to the eluting end of the column, and collecting the eluent. A combination of both positive and negative pressure may also be used.

The temperature used to contact the dairy source or cheese processing waste stream with the cation exchange resin is not particularly limited, so long as the temperature is not too high to cause decomposition of the components of the dairy source or waste stream. Generally ambient room temperature of from 17° C. to 25° C. is used.

Alternatively, the positively charged materials can be removed by such techniques as electrodialysis, ultrafiltration, reverse osmosis or salt precipitation.

After the optional treatment of the dairy source or cheese processing waste stream to remove the positively charged materials, the dairy source or cheese processing waste stream is contacted with an anion exchange resin.

Suitable anion exchange resins may be prepared by conventional techniques known to those of ordinary skill in the art. For example, a suitable anion exchange resin may be produced from a mixture of polymerizable monofunctional and polyfunctional monomer by radical emulsion polymerization techniques, then functionalized with strongly basic groups such as quaternary ammonium groups.

The degree of crosslinking in the anion exchange resin can be chosen, depending on the operating conditions of the to anion exchange column. A suitable resin may have from 2 to 12% crosslinking, preferably 8% crosslinking.

The particle size of the anion exchange resin is selected to allow for efficient flow of the dairy source or cheese processing waste stream, while still effectively removing the negatively charged materials. A suitable particle size for a column 30×18 cm is 100–200 mesh.

Suitable anion exchange resins include but are not limited to DEAE Sephadex, QAE Sephadex, DEAE Sepharose, Q Sepharose, DEAE sephacel, DEAE Cellulose, Ecteola Cellulose, PEI Cellulose, QAE Cellulose, Amberlite, Dowex 1-X2, Dowex 1-X4, Dowex 1-X8, Dowex 2-X8, Dowex Macroporous Resins, Dowex WGR-2, DEAE Trisacryl Plus-M, DEAE Trisacryl Plus-LS, Amberlite LA-2, AG 1-X2, AG 1-X4, AG 1-X8, AG 2-X8, AG MP-1 Resin, AG 4-X4, AG 3-X4, Bio-Rex 5 and ALIQUAT-336 (tricaprylylmethylammonium chloride from Henkel Corp.). More preferably suitable anion exchange resins are DOWEX TM 1×8 (a methylbenzyl ammonium linked to a polystyrene crosslinked resin from Dow Chemical) and AMBERLYSTE TM A-26, AMBERLITE TM IRA 400. AMBERLITE TM IRA 400, AMBERLITE TM IRA 416 and AMBERLITE TM IRA 910, strongly basic resins.

The dairy source or cheese processing waste stream can be contacted with the anion exchange resin, in any suitable manner which would allow the negatively charged materials to be absorbed onto the anion exchange resin. Preferably the anion exchange resin is loaded onto a column, and the dairy source or cheese processing waste stream is passed through the column, to absorb the negatively charged materials onto the resin.

An amount of anion exchange resin is selected to affect absorption of the negatively charged materials and will vary greatly depending on the dairy source or cheese processing waste stream being treated. Typically, when the waste stream is whey permeate, the loading ratio of cheese processing waste stream to anion exchange resin is from 5 to 200, preferably from 8–15, more preferably from 9 to 12:1 v/v. When contacting is affected in a column, the dairy source or cheese processing waste stream is preferably passed at a rate for from 1 to 70 cm/min, preferably from 2 to 15 cm/min, more preferably at a rate of 4.6 cm/min.

A suitable pressure may be selected to obtain the desired flow rate. Typically a pressure of from 0 to 100 PSIG is selected. Suitable flow rates may also be obtained by applying a negative pressure to the eluting end of the column, and collecting the eluent. A combination of both positive and negative pressure may also be used.

The temperature used to contact the dairy source or cheese processing waste stream with the anion exchange resin is not particularly limited, so long as the temperature is not too high to cause decomposition of the components of the dairy source or waste stream. The pH of the whey stream may also be adjusted in addition to the temperature. Generally ambient room temperature of from 17° to 25°0 C. and a pH of from 4 to 9 is used.

Upon contacting the eluent with the anion exchange resin, the negatively charged components of the dairy source or cheese processing waste stream are absorbed onto the anion exchange resin. The materials absorbed onto the anion exchange resin are negatively charged materials from a dairy source or cheese processing waste stream, which includes but is not limited to sialyloligosaccharides such as $\alpha(2-3)$ sialyllactose $\alpha(2-6)$ sialyllactose and (2-6) sialyllactosamine.

The resulting liquid, after contacting with the anion exchange resin, which contains primarily water and lactose may be dried and disposed of as animal feed, fertilizer or as a food supplement.

The anion exchange resin is then purged of the sialyloligosaccharide by eluting with an aqueous solution of a suitable salt such as sodium acetate, ammonium acetate, sodium chloride, sodium bicarbonate, sodium formate, ammonium chloride or a lithium salt such as lithium acetate, lithium bicarbonate, lithium sulfate, lithium formate, lithium perchlorate, lithium chloride and lithium bromide as an eluent. Purging an anion exchange resin with an aqueous salt can be accomplished by conventional means known to those of ordinary skill in the art. The sialyloligosaccharide can also be removed from the anion exchange resin with an aqueous alkali solution, although, the concentration of the aqueous alkali must be dilute enough so as not to destroy the structure of the sialyloligosaccharide. Suitable desorbing conditions can be determined through routine experimentation.

When eluted with an aqueous solution of lithium salts, no desalting by reverse osmosis is necessary. The entire eluent can be concentrated and dried, then the remaining solids washed with an organic solvent. The lithium salts are dissolved and the lithium salt of the sialyloligosaccharide remains as a solid. Specifically the lithium salts of $\alpha(2-3)$ sialyllactose, $\alpha(2-6)$ sialyllactose and $\alpha(2-6)$ sialyllactosamine have been found to have very low organic solvent solubility.

The lithium salts used in the eluent should be freely soluble in water, and have a high solubility in an organic solvent. In the context of the present invention, a high solubility in an organic solvent is $\geq 1$ gm of lithium salt per mL of organic solvent, preferably $\geq 5$ gm/mL, more preferably $\geq 10$ gm/mL at the temperature the solids are being washed. Suitable lithium salts which have been found to be freely soluble in water and have a high solubility in organic solvents include, lithium acetate, lithium bicarbonate, lithium sulfate, lithium formate lithium perchlorate, lithium chloride and lithium bromide.

The organic solvent used to wash the concentrated aluent should dissolve the eluting lithium salt, yet have a low solvating effect on the lithium salt of a sialyloligosaccharide. In the context of the present invention, a low solvating effect on the lithium salt of a sialyloligosaccharide is when the solubility of the lithium salt of the sialyloligosaccharide is $\leq 0.5$ gm per mL of organic solvent, preferably $\leq 0.25$ gm/mL, more preferably $\leq 0.1$ gm/mL at the temperature the solids are being washed. Suitable solvents include but are not limited to acetone, methyl ethyl ketone, 3-pentanone, diethyl ether, t-butyl methyl ether, methanol, ethanol and a mixture thereof.

The organic solvent preferably contains $\leq 0.1\%$ wt., more preferably $\leq 0.01\%$ wt. of water, most preferably the organic solvent is anhydrous. The use of an organic solvent containing high concentrations of wateir, results in dissolution of the lithium salts of the sialyloligosaccharide. The temperature of the organic solvent is not particularly limited, however preferably the organic solvent is at room temperature or below, more preferably 0°–5° C.

Due to the high hygroscopicity of the lithium salts of the sialyloligosaccharide, washing of the solids are conducted under conventional conditions which are known to those of ordinary skill in the art, to limit the absorption of atmospheric moisture. For example such washing can be conducted under an inert atmosphere, in a dry box or using a Schlenk-type apparatus.

When purging the anion exchange resin, with an eluent, a suitable purging solution is 50 mM. The pH of the eluent is preferably adjusted to be from 4 to 9, more preferably from 5 to 6. Generally from 2 to 5, preferably 4 column volumes of purging solution are used to remove the sialyloligosaccharides from the anion exchange resin, preferably performed at ambient temperature. Preferably, lithium acetate is used to purge the anion exchange resin of the sialyloligosaccharides.

The sodium salt of the sialyloligosaccharide can be obtained by conventional ion-exchange techniques, known to those of ordinary Skill in the art.

When an eluent other than a lithium salt is used to remove the sialyloligosaccharides from the anion exchange resin, the eluent containing the sialyloligosaccharides and the salt, can be concentrated and desalted, such as by subjecting the eluent to reverse osmosis to remove the salt from the sialyloligosaccharide. Reverse osmosis can be conducted through a membrane with a 100 to 700 Dalton molecular weight cut off, preferably a 400 Dalton cut-off.

Reverse osmosis is preferably conducted at a pressure of from 300–1,600 psi, more preferably from 400–600 psi, even more preferably at a pressure of 450 psi.

After the salts have been removed by reverse osmosis, the resulting material can be concentrated to provide a solid material containing gialyloligosaccharides such as $\alpha(2-3)$ sialyllactose and $\alpha(2-6)$ sialyllactose, which can be recrystallized from a mixture of water and organic solvents.

Preferably precipitation solvents are selected from the group of ethanol, acetone, methanol, isopropanol, diethyl ether, t-butyl methylether, ethyl acetate, hexane, tetrahydrofuran and water.

In addition, the eluent, from the aniqn exchange column, which contains a mixture of sialyloligosaccharides which includes $\alpha(2-3)$ sialyllactose, $\alpha(2-6)$ sialyllactose and $\alpha(2-6)$ sialyllactosamine, can be subjected to separation of the sialyloligosaccharides contained therein, by column chromatography on a DOWEX 1×2 anion exchange resin, at pH 4 to 6 using a buffer a suitable salt such as sodium acetate, ammonium acetate or a lithium salt such as lithium acetate, lithium perchlorate, lithium chloride and lithium bromide as an eluent. A solution of lithium acetate is preferred.

Suitable anion exchange resins may be prepared by conventional techniques known to those of ordinary skill in the art as previously described.

The degree of crosslinking in the anion exchange reain can be chosen, depending on the operating conditions of the anion exchange column. A suitable resin may have from 2 to 12% crosglinking, preferably 2% crosslinking.

The particle size of the anion exchange resin is selected to allow for efficient flow of the dairy source or cheese processing waste stream, while still effectively affecting chromatographic separation of the negatively charged materials. A suitable particle size for a column 20×100 cm is 200–400 mesh.

Suitable anion exchange resins include but are not limited to DEAE Sephadex, QAE Sephadex, DEAE Sepharose, Q Sepharose, DEAE Sephacel, DEAE Cellulose, Ecteola Cellulose, PEI Cellulose, QAE Cellulose, Amberlite, Dowex 1-X2, Doupex 1-X4, Dowex 1-X8, Dowex 2-X8, Dowex Macroporous Resins, Dowex WGR-2, DEAE Trisacryl Plus-M, DEAE Trisacryl Plus-LS, Amberlite LA-2, AG 1-X2, AG 1-X4, AG 1-X8 AG 2-X8, AG MP-1 Resin, AG 4-X4, AG 3-X4, Bio-Rex 5 and ALIQUAT-336 (tricaprylylmethylammonium chloride from Henkel Corp.). Preferred resins are DOWEX 1×2 (a tri-methylbenzyl ammonium linked to a polystyrene crosslinked resin from Dow Chemical) and AMBERLYST and AMBERLYTE basic resins.

The mixture of sialyloligosaccharides to be separated are subjected to column chromatography on an anion exchange resin. An amount of anion exchange resin is selected to affect separation of the different sialyloligosaccharides. Typically the loading ratio of sialyloligosaccharide to anion exchange resin is from 0.1 to 5, preferably from 0.2 to 4, more preferably 1 grams of material per liter of resin at a loading concentration of from 0 to 10 mM of salt. The chromatography is conducted at a rate of from 1 to 20 cm/h, preferably 4.6 cm/h superficial velocity. A suitable pressure may be selected to obtain the desired flow rate. Typically a pressure of from 0 to 22 PSIG is selected. Suitable flow rates may also be obtained by applying a negative pressure to the eluting end of the column, and collecting the eluent. A combination of both positive and negative pressure may also be used.

Any temperature may be used to contact the dairy source or cheese processing waste stream with the anion exchange resin, so long as the temperature is not too high to cause decomposition of the components of the sialyloligosaccharides. Generally ambient room temperature of from 17° to 25° C. is used.

When the buffer eluent is a lithium salt, the individual sialyloligosaccharides can be isolated by concentrating the eluent to form a solid and washing the lithium salts away with an organic solvent. Isolation of the lithium salt of a sialyloligosaccharide from a lithium salt eluent is as previously described.

The sodium salt of the sialyloligosaccharide can be obtained by conventional ion-exchange techniques, known to those of ordinary skill in the art.

When the buffer eluent is not a lithium salt, the individual sialyloligosaccharides can be isolated by reverse osmosis techniques.

According to another embodiment of the present invention, a dairy source or cheese processing waste stream can be treated without using an ion-exchange column and without using reverse osmosis.

According to this embodiment, a dairy source or cheese processing waste stream is contacted with a solvent, wherein sialyloligosaccharides are extracted.

The sialyloligosacoharides which are extracted include but are not limited to α(2–3) sialyllactose, α(2–6) sialyllactose and α(2–6) sialyllactosamine.

A dairy source or cheese processing waste stream can be contacted with a solvent in any suitable manner to effectively extract, by solubilization, sialyloligosaccharides.

For example solid lactose, in powder form can be packed into a column, and a solvent passed through the packed column. As the solvent passes through the column, the sialyloligosaccharides are extracted from the solid lactose. To improve the solubilization of sialyloligosaccharide, the solvent can be recirculated through the column, until an equilibrium concentration of sialyloligosaccharide is obtained in the solvent.

To improve the solubilization of sialyloligosaccharide, the solvent can be recirculated at elevated temperature, below the thermal decomposition point of the sialyloligosaccharides, preferably from 27° C. to 80° C., more preferably from 60° C. to 75° C., at ambient pressure.

A dairy source or cheese processing waste stream, can also be contacted with a solvent, as a slurry or suspension of the dairy source or cheese processing waste stream in the solvent. The dairy source or cheese processing waste stream is mixed with the solvent, preferably in a 1:4 v/v ratio, more preferably 1:3 v/v. The slurry or suspension is then stirred until the sialyloligosaccharides are solubilized in the solvent.

The ratio of dairy source or cheese processing waste stream to solvent is selected so as to maximize the amount of recovered sialyloligosaccharide and minimize the amount of solvent used. Due to the high solubility of sialyloligosaccharides in the solvent chosen, the amount of solvent is typically much less than the volume of dairy source or cheese processing waste stream. Accordingly when lactose is being processed, it is not necessary for the lactose to be completely dissolved.

The suspension can be stirred at any temperature, below the thermal decomposition point of the sialyloligosaccharides, preferably from 4° C. to 80° C. more preferably from 4°–27° C., at ambient pressure.

Suitable solvent systems are, water, C[1–5] alcohols, such as methanol, ethanol, n-propanol, iso-propanol, n-butanol, iso-butanol, sec-butanol, tert-butanol, tert-amyl alcohol and iso-amyl alcohol and a mixture thereof. The amount of water in the C[1–5] alcohol solvent system will vary depending on the alcohol used. Preferably the solvent contains from 0–75% water (v/v), more preferably from 20–70% water (v/v), more preferably from 44–66% water. A particularly preferred solvent system is an aqueous ethanol solvent containing from 44–66% water.

When elevated temperature is used, it is preferred to remove the solvent from the column, slurry or suspension after the maximum concentration of sialyloligosaccharide is reached, followed, by cooling of the separated solvent. Upon cooling of the separated solvent, solubilized lactose will crystallize out and can be removed from the solvent containing the sialyloligosaccharide, by conventional means such as filtration, centrifugation and decanting.

An aqueous solution of lactose such as the mother liquor obtained by crystallizing lactose, can also be treated with a solvent at elevated temperature, preferably from 60° to 75° C., more preferably from 68° to 72° C., followed by cooling and precipitation of the lactose from solution. separation of the precipitated lactose from the solvent and concentration of the solvent provides the sialyloligosaccharide.

The aqueous solution of lactose and the solvent are mixed in a ratio of about 1:3 v/v, preferably 1:2 v/v more preferably 1:1 v/v. A suitable solvent for treating an aqueous solution of lactose is a C[1–5] alcohol.

The separated solvent, or column eluent can be concentrated to yield high purity sialyloligosaccharide. This material can be further purified by recrystallization from aqueous ethanol and a suitable organic solvent, to remove lactose impurity.

In another embodiment to the column, slurry or suspension treatment technique, a portion of the extraction solvent can be removed and passed through an anion exchange column and the solvent returned to the system. In this fashion, the sialyloligosaccharide can be concentrated on the anion exchange column. The solvent to be passed through the anion exchange resin can be removed continuously or batch wise.

Once the anion exchange column has been saturated with sialyloligosaccharide, the column can be removed from the system and purged to obtain sialyloligosaccharide. A suitable purging solution is 120 mM LiOAc. Generally from 2 to 5, preferably 4 column volumes of purging solution are used to remove the negatively charged materials from the anion exchange resin, performed at ambient temperature. Suitable anion exchange resins, contacting conditions and purging conditions have been previously described above.

Sialyloligosaccharides may also be extracted from whey waste streams using supercritical $CO_2$ extraction techniques, in a method analogous to the methods used to extract caffeine from coffee beans. A technique for the extraction of caffeine from coffee beans using moist supercritical $CO_2$ is described in U.S. Pat. Nos. 3,806,619 and 4,260,639. In general, the supercritical $CO_2$ extraction method comprises contacting lactose or an aqueous solution of lactose with supercritical $CO_2$, under conditions to effect solubilization of sialyloligosaccharides by the supercritical $CO_2$. The supercritical $CO_2$, containing sialyloligosaccharides is separated from the lactose or aqueous solution of lactose, then the $CO_2$ is removed by evaporation, leaving behind the extracted sialyloligosaccharides.

Whey containing sialic acids, is a byproduct obtained when cheese or rennet casein is produced from milks such as cow milk, goat milk and sheep milk. Due to the fat in dairy sources and the small amount of curd or fat often remains in milk whey, it is preferable that the fat content of these compositions generated according to the method of the invention be previously removed by a cream separator or clarifier. In order for milk whey proteins such as beta -lactoglobulin to be efficiently adsorbed to a cation exchanger, the dairy source or whey may be previously concentrated with an ultrafiltration device. Further, the dairy source or whey may be previously desalted with an electric dializer and/or an ion exchange resin.

The dairy source or whey is adjusted to a pH of 2–5 before it is subjected to the cation exchanger. As materials for adjusting the pH, any kind of materials may be used. For example, they include an acid such as hydrochloric acid, sulfuric acid, acetic acid, tactic acid and citric acid. Alternatively, acidified whey which has been desalted with the resin to have a pH of about 1–4, may be used for adjusting the pH, in order that the whey contains a high content of sialic acids. In the dairy source or whey which has been adjusted to a pH of 2–5, sialic acids are negatively, charged, while most part of dairy source or whey protein is positively charged. When this dairy source or whey is contacted with the cation exchanger, dairy source or whey protein is selectively adsorbed to the cation exchanger and, as a result, sialic acids are selectively recovered as an exchanger-passed solution. If the pH of the dairy source or whey is higher than 5, sialic acids and most part of dairy source or whey protein are negatively charged. Therefore, the separation is not efficient, although these two can be separated with an anion exchanger utilizing difference in adsorption. If the pH of the dairy source or whey is lower than 2, sialic acids decompose and therefore the process is not practical.

The cation exchanger-passed solution obtained according to this embodiment may optionally be concentrated, desalted and/or dried using techniques known in the art. In addition, a mother liquor obtained after the exchanger-passed solution is concentrated and then crystallized to remove lactose may be used as a material having a high content of sialic acids. The concentration may be made by an evaporator. The crystallization may be made by cooling or by addition of a seed crystal.

In order to obtain a much higher sialic acids content composition, it is preferable that the pH of the exchanger-passed solution and/or its mother liquor be adjusted before they are concentrated and/or desalted. The concentration may be made by evaporation or by ultrafiltration. The desalting may be made by electric dialysis, ion exchange, ultrafiltration or diafiltration. The diafiltration is a technique for further increasing the protein content, wherein a liquid, which has been concentrated to some extent, is ultrafiltrated while simultaneously water is added thereto and a passing solution is withdrawn. When the exchanger-passed solution and/or its mother liquor is adjusted to a pH of 4 or higher, the concentration may be made by ultrafiltration using an ultrafiltration membrane having a cutoff molecular weight of 2,000 approximately equal to 50,000 Dalton. The concentration may be also made by the ultrafiltration using an ultrafiltration membrane having a cutoff molecular weight of 10,000 at a pH of 4 or lower. In other words, kappa-casein glycomacropeptide (GMP) as a sialic acid is present as a monomer at a pH of 4 or lower, while it associates into a multimonomer at a pH of above 4. As materials for adjusting the pH, any kind of materials may be used. They include alkalis such as sodium hydroxide, potassium hydroxide, calcium hydroxide, potassium carbonate, sodium citrate, etc.

The concentrate thus obtained is a composition having a high content of sialic acids such as GMP. Incidentally, alpha-lactalbumin, which is usually contained in milk whey together with sialic acids, may be separated from sialic acids, for example, by ultrafiltering the exchanger-passed solution or its mother liquor at a pH of 4 or higher using an, ultrafiltration membrane having a cutoff molecular weight of 2,000 to 50,000 Dalton.

5.5. Transgenic Mammals Producing Milk Enriched For α(2–3) Sialyllactose

The α(2–3) sialyllactose content in milk may also be enriched by expressing α(2–3) trans-sialidase, derivatives, and analogs (see Section 5.1) in transgenic mammals. In one embodiment, transgenic mammals of the invention comprise an α(2–3) trans-sialidase encoding sequence that has been operably linked to a regulatory sequence of a gene expressed in mammary tissue. Similarly, the invention provides for methods for enriching for α(2–3) sialyllactose in milk comprising the steps of introducing a transgene comprising an α(2–3) trans-sialidase encoding sequence operably linked to a regulatory sequence of a gene expressed in mammary tissue into the germline of a mammal to produce a transgenic mammal; selecting a transgenic mammal demonstrating α(2–3) trans-sialidase activity; and obtaining milk from the selected transgenic mammal.

The α(2–3) trans-sialidase transgenes introduced into the transgenic animals of the invention comprise nucleotide sequences encoding α(2–3) trans-sialidase, derivatives or analogs (as described supra in Section 5.1) operably linked to regulatory sequences (i.e., inducible and non-inducible promoters, enhancers, operators and other elements which drive and/or regulate expression) of a gene expressed in mammary tissue. The nucleotide coding sequence used to produce the transgenic animals of the invention may be regulated by any suitable regulatory sequences, but preferred are mammalian milk protein promoter and/or regulatory nucleotide sequences. Regulatory sequences from milk-specific protein genes which may be used to drive expression of the target sequence include, but are not limited to, promoters derived from: whey acidic protein, β-lactoglobulin, α-lactalbumin, αsl-casein, and β-casein. See e.g., Colman, A., 1996, *Am. J. Clin. Nutr.* 63:639S–645S (citing Houdebine, 1994, *J. Biotechnol.* 43:269–87).

Many nucleotide sequences of regulatory sequences from genes expressed in mammary tissue are known (see e.g., Houdebine, 1994, *J. Biotechnol.* 43:269–87). Alternatively, regulatory sequences contained in genomic nucleotide sequences of genes known to be expressed in mammary tissue may be identified using techniques known in the art. For example, the genomic nucleotide sequences located upstream of the coding sequence of the gene expressed in mammary tissue can be cloned adjacent to a reporter gene, such as, for example, a chloramphenicol acetyl transferase (CAT) gene. The genomic sequence/reporter gene construct is then introduced into a mammal using techniques known in the art (See e.g., Section 5.5.1) and the presence of regulatory sequences in the genomic sequence/reporter gene construct is indicated by reporter gene activity, which is assayed using techniques known in the art. To more precisely define the regulatory elements, deletion mutants can be generated and tested for reporter gene activity.

The regulatory sequences of the α(2–3) trans-sialidase transgene may include the entire, or any portion of, the promoters, enhancers or their corresponding genes. For example, the α(2–3) trans-sialidase/regulatory sequence transgene construct of the invention may comprise the nucleotide coding sequence for the entire mammalian milk protein, or any portion thereof, fused in the correct coding frame to the α(2–3) trans-sialidase encoding nucleotide sequence. The expression of these chimeric constructs may be regulated by the regulatory sequence of the mammalian milk gene component of the chimeric or alternatively, by the regulatory sequence of another gene that is expressed in mammary tissue.

Additionally, the nucleotide regulatory sequences of the α(2–3) trans-sialidase transgene gene constructs, include but are not limited to, the entire, or any portion of the endogenous milk protein promoter of the founder animal into which the α(2–3) trans-sialidase gene is being introduced.

Regulatory nucleotide sequences may be obtained from mammalian milk protein genomic DNA using techniques known in the art, including, but not limited to, PCR and hybridization screening of genomic libraries, as further described in Section 5.1. For a review of techniques which may be used, see e.g., Sambrook et al., 1989, Molecular Cloning, A Laboratory Manual, 2nd Ed. Cold Spring Harbor Laboratory Press, NY). These techniques may additionally be applied to generate the α(2–3) trans-sialidase/regulatory transgene of the invention and to engineer chimeric gene constructs that utilize regulatory sequences other than the mammalian milk protein regulatory sequences. Additionally, methods which have been applied to construct transgenes that have successfully expressed proteins in the milk of transgenic mammals may routinely be modified to generate the α(2–3) trans-sialidase transgenic mammals of the invention. See e.g., Wright et al., 1991, *Biotechnology* (NY) 9:830–834; Carver et al., 1993, *Biotechnology* (NY) 11:1263–1270; Clark et al., 1989, *Biotechnology* (NY) 7:487–492); Velander et al., 1992, *Proc. Natl. Acad. Sci. USA,* 89:12003–12007; and Ebert et al., 1991, *Biotechology* (NY) 9:835–838, the contents of each of which is incorporated by reference herein in its entirety.

5.5.1. Production of Tranagenic Animals

Mammals of any species, including but not limited to, sheep, goats, pigs and cows and non-human primates, e.g., baboons, monkeys, and chimpanzees, may be used to generate α(2–3) trans-sialidase transgenic animals of the invention. Any technique known in the art may be used to introduce the transgene into animals to produce the founder lines of transgenic animals. Such techniques include, but are not limited to, pronuclear microinjection (Paterson et al., 1994, *Appl. Microbiol. Biotechnol.* 40:691–698; Carver et al., 1993, *Biotechnology* (NY) 11:1263–1270; Wright et al. 1991 *Biotechnology* (NY) 9:830–834; and Hoppe et al., 1989, U.S. Pat. No. 4,873,191); retrovirus mediated gene transfer into germ lines (Van der Putten et al., 1985, *Proc. Natl. Acad. Sci., USA* 82, 6148–6152), blastocysts or embryos; gene targeting in embryonic stem cells (Thompson et al., 1989, *Cell* 56:313–321); electroporation of cells or embryos (Lo, 1983, *Mol Cell. Biol.* 3:1803–1814); introducing nucleic acid constructs into embryonic pleuripotent stem cells and transferring the stem cells back into the blastocyst; and sperm-mediated gene transfer (Lavitrano et al., 1989, *Cell* 57:717–723); etc. For a review of such techniques, see Gordon, 1989, "Transgenic Animals," *Intl. Rev. Cytol.* 115, 171–229, which is incorporated by reference herein in its entirety.

Any technique known in the art may be used to produce transgenic clones containing a trans-sialidase gene, for example, nuclear transfer into enucleated oocytes of nuclei from cultured embryonic, fetal, or adult cells induced to quiescence (Campell et al., 1996, *Nature* 380:64–66; Wilmut et al., 1997, *Nature* 385:810–813).

In addition, α(2–3) trans-sialidase transgene expression may be accomplished by removing mammary secretory epithelium from the animals, transfecting the epithelial cells with a transqenic construct, and reintroducing the transfected epithelial cells into the animal during the prepartum period so that the target gene is expressed in the subsequent lactation period. See e.g., Bremel et al., 1989, *J. Dairy Sci.* 72:2826–2833. While this method has the disadvantage of providing transient expression of α(2–3) sialyllactose, as the mammary secretory epithelium is sloughed off during the drying off period, this technology provides a method by which to accomplish the goal of enriching α(2–3) sialyllactose concentrations in milk without the significant time investment of creating transgenic animals.

Once the founder animals are produced, they may be bred, inbred, outbred, or crossbred to produce colonies of the particular animal. Examples of such breeding strategies include but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines.

The present invention provides for transgenic animals that carry the tranagene in all their cells, as well as animals which carry the transgene in some, but not all their cells, i.e., mosaic animals. The transgene may be integrated as a single transgene or in concatamers, e.g., head-to-head tandems or head-to-tail tandems.

5.5.2 Screening of Transgenic Animals

The transgenic animals that are produced in accordance with the procedures detailed in Section 5.5.1 are preferably screened and evaluated to select those animals which may be used as suitable producers of milk containing enriched concentrations of α(2–3) sialyllactose when compared to non-transgenic animals.

Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR) and the like.

The transgenic animals that express α(2–3) trans-sialidase protein (detected immunocytochemically, using antibodies directed against α(2–3) trans-sialidase) at easily detectable levels may serve as suitable producers of milk containing enriched concentrations of α(2–3) sialyllactose.

5.5.3 α(2–3) Sialyllactose Enrichment in the Milk of Transgenic Mammals

The invention provides for a method for enriching for α(2–3) sialyllactose in milk comprising the steps of introducing a transgene comprising an α(2–3) trans-sialidase encoding sequence operably linked to a regulatory sequence of a gene expressed in mammary tissue into the germline of a mammal to produce a transgenic mammal; selecting a transgenic mammal demonstrating α(2–3) trans-sialidase activity; and obtaining milk from the selected transgenic mammal. The α(2–3) sialyllactose produced according to this invention is also encompassed by the invention.

α(2–3) sialyllactose enriched according to the method of the invention may be recovered using techniques known in the art as well as those described infra (see Section 5.4).

In specific embodiments, the α(2–3) sialyllactose is recovered from the milk of the selected transgenic mammal prior to, during, or after processing of the milk. In a preferred embodiment the α(2–3) sialyllactose is recovered from the milk of the selected transgenic mammal after the milk has been subjected to processing (e.g., a cheese processing waste stream derived from this milk). The invention is further illustrated by reference to the following examples. It will be apparent to those of skill in the art that many modifications, both to materials and methods, may be practiced without departing from the purpose and scope of this invention.

5.6 Example: Isolation and Cloning of a DNA Sequence Encoding α(2–3) Trans-sialidase Activity In this Example, a chimeric DNA sequence was cloned using the polymerase chain reaction (PCR) and *Trypanosoma cruz* α(2–3) trans-sialidase DNA as template. Site directed mutagenesis was applied to alter this sequence to encode a tyrosine at position 342 in place of the histidine initially encoded at this position. The mutated sequence was cloned into a pGEX expression plasmid, transformed into a host cell, and expressed as a glutathione-S-transferase fusion protein having α(2–3) trans-sialidase activity.

Two sets of oligonucleotide primers (e.g., PCR Primer Set #1 and PCR Primer Set #2) were synthesized for use in PCR to enzymatically amplify an α(2–3) trans-sialidase encoding sequence from *T. cruzi* genomic DNA.

PCR Primer Set #1 was designed to amplify a region of the nucleic acid sequence that encodes the amino-terminal region of the *T. cruzi* trans-sialidase that maintains the active domain for α(2–3) trans-sialidase activity. In order to subsequently directionally clone the amplified fragment, the 5'-primer was designed to include a recognition sequence for an a unique restriction endonuclease (i.e., Xba I) at the 5' end of the amplified fragment. The sequences of 5' primer and 3' primer of Set #1 were (SEQ ID NO:5 and SEQ ID NO:6):

ts1xba-5':
5'-TTTTCTAGAATGCTGGCACCCGGATCGAGC-3' ts1-3':
5'-CTGTGCGACAAAAAGCCAACAAGACCAACC-3'

PCR Primer Set #2 was designed to amplify a region of the nucleic acid sequence that encodes the carboxyl-terminal region of the *T. cruzi* α(2–3) trans-sialidase and which overlapped the fragment amplified by PCR Primer Set #1. The 3'-primer was designed to include a recognition sequence for an another unique restriction endonuclease (i.e., Xho I) at the 3' end of the amplified fragment. The sequences of 5' primer and 3' primer of Set #2 were (SEQ ID NO:7 and SEQ ID NO:8):

ts2-5':
5'-ACTGAACCTCTGGCTGACGGATAACCAGC-3' ts2xho-3':5'-
TTTCTCGAGTCAGGCACTCGTGTCGCTGCT-3'

PCR techniques known in the art were used to amplify DNA fragments generated using each of these primer sets and *T. cruzi* genomic DNA as template.

The DNA fragments generated from the PCR of the primers of Set #1 and the primers of Set #2 were joined to generate the full-length fragment of the α(2–3) trans-sialidase using the following procedure. The DNA fragment generated from the PCR of the primers of Set #1 was digested with the restriction endonucleases XbaI and PstI. The DNA fragment generated from the PCR of the primers of Set #2 was digested with XhoI and PstI. The PstI site was contained in a region that both PCR products had in common. The digestion of the PCR products generated “sticky ends” on the products. The XbaI site at the 5' end of the DNA fragment generated from the PCR of the primers of Set #1 and the XhoI site at the 3' end of the DNA fragment generated from the PCR of the primers of Set #2 were designed to be used in the directional cloning of the entire sequence into the appropriate expression plasmid. Both PCR products were then ligated together into Xba I/Xho I-digested pGEX (Pharmacia, Piscataway, N.J.) plasmid which contains the same restriction endonuclease sites in its polylinker region. The α(2-3) trans-sialidase nucleotide sequence was directionally cloned in-frame of the pGEX fusion gene, glutathione-S-transferase. The trans-sialidase pGEX construct was then transformed into host cells using techniques known in the art.

DNA Sequence analysis revealed that the procedure described in this example resulted in the cloning of an α(2-3) trans-sialidase which contained a $Tyr^{342}$→His mutation and was thus inactive (hereinafter, this clone will be referred to as “pGEX-TS/His”). Therefore, a site directed mutagenesis protocol was followed which changed $His^{342}$→Tyr.

Site-directed mutagenesis was accomplished using the following method. A set of oligonucleotide primers (“mut-5'” and “mut-3'”) were designed to mutate $His^{342}$ to $Tyr^{342}$ in order to generate an active trans-sialidase. The sequences of mut-5' and mut-3' were SEQ ID NO:9 and SEQ ID NO:10):

mut-5':
5'-GGGCAAGTATCCATTGGTGATGAAAATTCCG CCTACAGCT-3' mut-3':
5'-TACAGCTTATCATCCTTGTACAGGACGGAGCT GTAGGCGG-3'

The mut-5' and mut-3' primers were used in conjunction with the PCR primers from PCR Primer Sets #1 and #2 to amplify overlapping DNA fragments encoding the α(2-3) trans-sialidase using pGEX-TS/His as a template. The primers were designed to amplify two fragments that overlapped by 65 nucleotides and to include PCR-directed mutations of the $His^{342}$ codon which would ultimately encode a $Try^{342}$. The new overlapping fragments were gel-purified, and used in a PCR reaction as both primer and template. That is, the two fragments were mixed together, heat-denatured and allowed to re-anneal in a PCR primer-free PCR reaction (which allows annealed fragments to be end-filled). The 5'-end primer from PCR Primer Set #1 and the 3'-end primer from PCR Primer Set #2 were then added to the mixture to amplify the full-length, mutated trans-sialidase-encoding fragment. The new fragment was then ligated into pCEX as described above and used to transform E. coli BL21 cells (hereinafter, this clone will be referred to as "pGEX-TS/Tyr").

E. coil bearing pGEX-TS/Tyr were expressed and assayed for α(2-3) trans-sialidase activity using techniques known in the art. Clones expressing α(2-3) trans-sialidase activity were isolated and utilized in the lysate preparations utilized to generate the data presented in FIGS. 5–9 and Sections 5.7 and 5.8.

5.6.1 Preparation of T. cruzi α(2-3) trans-sialidase lysates

A single colony of E. coli BL21 cells carrying pGEX-TS/Tyr was inoculated into 2 ml of LB medium (tryptone, yeast. extract, NaCl) containing an appropriate antibiotic and the bacterial culture was incubated at 37° C. in a shaking incubator overnight. The next day, one liter of LB medium containing the appropriate antibiotic was inoculated with 50 μl of the overnight bacterial culture, and the culture was incubated at 37° C. in a shaking incubator until the culture's $O.D._{600}$=1.0. The bacteria in the 1 L culture was induced to express the α(2-3) trans-sialidase by the addition of isopropylthio-β-D-galactoside (IPTG) to a final concentration of 100 μM. The induced 1 L culture was then placed in a shaking incubator at 20° C. overnight.

The next day, the bacteria cells were collected by centrifugation, and a bacterial lysate was prepared using an APV Gaulin homogenizer. The homogenizer uses high pressure (10,000 psi) to lyse the cells. Alternatively, a DynoMill, french press, $N_2$ cavitation, douncer, freeze thawing or similar tool may be used.

Alternatively, the α(2-3) trans-sialidase enzyme may be expressed using other methods known in the art, including, but not limited to, secretory expression in E. coli, expression in fungi and expression in insect cells.

5.7 EXAMPLE: ENRICHMENT AND ISOLATION OF α(2-3) SIALYLLACTOSE IN MILK PRIOR TO CHEESE MANUFACTURING

In this Example, the addition of T. cruzi α(2-3) transsialidase to raw milk prior to the use of this milk in the manufacture of a rennet cheese, is demonstrated to result in an enrichment of α(2-3) sialyllactose.

5.7.1 Materials and Methods

Sixty-seven gallons of fresh, raw milk were collected in 7 milk cans and chilled to 37° F. Twenty thousand units of α(2-3) trans-sialidase were added to each milk can. One unit of α(2-3) trans-sialidase=1 μmol NAN-α(2-3)-Gal-β(1-4)-GlcNAc-β(1-3)-Gal-β(1-4)-Glc (LST-d) produced/min in the standard assay using α(2-1) sialyllactose and Gal-β(1-4)-GlcNAc-β(1-3)-Gal-β(1-4)-Glc (lacto-N-neotetraose, LNnT) as substrates. In this particular Example, a filtered/frozen/thawed E. coli lysate containing 400 units/ml α(2-3) trans-sialidase was used. The milk containing the α(2-3) trans-sialidase was incubated at 50° F. for 12 hours. Samples were collected from 2 of the milk cans at 0, 1, 2, 3, and 11 hours of the incubation and analyzed for α(2-3) sialyllactose.

After the 12 hour incubation, the milk was pasteurized by continuous HTST at 161° F. for 18 seconds and cooled to 80° F. according to standard procedure. See Kosikowski, Frank V.; 1977, Cheese and Fermented Foods, 2nd edition, Edwards Brothers Publishing, Ann Arbor, Mich. The milk was collected in a "double circle" vat and processed for white cheddar cheese according to standard procedure.

5.7.1.1 Cheese Making Protocol

At Time=0, ten grams of a 33 g freeze-dried lactic acid culture (EZAL EZ100 5000#, Lot No. 93053A, Rhone Polenc) were added to the pasteurized milk and the temperature was raised to 88° F. Three ounces of 0.02% $CaCl_2$ (Rhone Polenc) were added. The culture was stirred constantly at 12 rpm and the temperature was held constant at 88° F. for 1 hour. The acidity of the solution was 0.17.

At Time=1 hour and 15 minutes, milk coagulator was added. Two ounces of a 50,000 MCU/ml Chymax solution were added to the 480# of fermented milk (3 oz of the Chymax solution are recommended/1000# (the Pfizer brand contains chymosin, NaCl and propylene glycol). The solution was mixed, for 30 seconds and then allowed to set for30 minutes. During this stage, the milk was observed to have coagulated, forming a yogurt/sour cream-like consistency anid the titratable acidity dropped to 0.10.

At Time=1 hour and 45 min, the curd was cut into 1 cm cubes using two knives over a period of 10 minutes.

At Time=1 hour and 55 minutes, the temperature was raised 2° F. every 5 minutes until the temperature reached 102° F. The temperature was then held at 102° F. with constant stirring. After 30 minutes of cooking, the stir paddles were replaced with stirring rakes and the whey was allowed to drain. Eight liters of whey were collected for analysis. The pH began to drop from the current 6.5 level, and the titratable acidity began to rise from 0.10.

At Time=6 hour and 20 minutes, the pH of the whey had dropped to 5.85. The acidity had risen to 0.285 and the pH of the whey had dropped to 5.85. While a lower pH and higher acidity (up to 0.6) are desired, it is believed that the use of an older freeze-dried lactic acid culture was the reason for the higher pH and lower acidity levels observed in this example. The curd was salted (1.25# of salt into 44# of curd), stirred and then pressed overnight at room temperature. The curd was stored at 50° F. for 6 months.

5.7.1.2 Sample Dry Weight Analysis

Five ml of either the milk or whey samples were placed in pre-weighed aluminum weigh boats and placed in an 85° C. vacuum oven (<3 mmHg) overnight. The samples were then weighed and returned to the oven for an additional 2 hours. The weighing process was repeated every 2 hours until 2 consecutive, consistent readings were obtained. The net weight of the dried sample was expressed in terms of % weight per volume of sample. The results are shown in Table 1.

5.7.1.3 α(2-3) Trans-sialidase Reaction

The milk and whey samples were frozen immediately upon collection. For analysis, frozen samples were thawed quickly, boiled to coagulate the remaining protein and centrifuged at 10,000×g in a microcentrifuge for 10 minutes. The supernatant was collected and filtered through a 10,000

MW filter to separate the α(2-3) sialyllactose from the remaining higher molecular weight compounds as a preparation for high performance liquid chromatography (HPLC). The amount of α(2-3) sialyllactose in the milk samples was quantified by HPLC and the values were expressed in terms of total dissolved solids.

5.7.2 Results

As demonstrated by the data presented in Table 1, the α(2-3) trans-sialidase treatment resulted in a significant increase in a α(2-3) sialyllactose within the first hour of inoculation. This level of activity most probably was maintained throughout the entire 11 hour incubation period. The fluctuation in α(2-3)sialyllactose levels after the first hour was attributed to the difficulty in obtaining homogenous samples from the milk cans. Interestingly, a large increase in α(2-3) sialyllactose concentration was observed in the whey after the curd dropped from the milk. The end result was α(2-3) trans-sialidase treatment of milk prior to cheddar cheese production resulted in a 2 to 4 fold increase in α(2-3) sialyllactose when compared to other whey samples the dairy source of which had not been previously treated with α(2-3) trans-sialidase. The addition of α(2-3) trans-sialidase to the raw milk did not have any untoward effect upon the taste or quality of the cheese generated using the α(2-3) trans-sialidase treated milk.

Effect of α(2-3) trans-sialidase treatment of milk prior to cheddar cheese production

| Sample | α(2-3) sialyllactose (μg/ml) | % Dry Weight | % α(2-3) sialyllactose per gram of solid |
|---|---|---|---|
| Milk Time = 0 | 37 | 12.94 | 0.02 |
| Milk Time = 1 hr | 172 | 10.03 | 0.17 |
| Milk Time = 2 hr | 160 | 11.52 | 0.14 |
| Milk Time = 11 hr | 181 | 11.55 | 0.16 |
| Whey | 255 | 8.91 | 0.29 |
| Whey | 244 | 7.84 | 0.31 |
| Whey | 239 | 8.42 | 0.28 |
| Standard dry whey | — | — | 0.06–0.13 |

5.8 EXAMPLE: ENRICHMENT OF α(2-3) SIALYLLACTOSE IN DAIRY SOURCES AND CHEESE PROCESSING WASTE STREAMS

This Example investigates the enrichment of α(2-3) sialyllactose in dairy sources and cheese processing waste streams that have been contacted with bacterial lysates containing α(2-3) trans-sialidase activity. Bacterial lysates were prepared as set forth infra in Section 5.6. Methods for producing and assaying for α(2-3) sialyllactose were essentially as set forth infra in Section 5.3.

As shown in FIG. 5, the addition of α(2-3) trans-sialidase increased α(2-3) sialyllactose concentrations over a incubation mixture pH range of 4.0–9.0.

Increased α(2-3) sialyllactose concentrations of 2–5 fold were observed in dairy sources and cheese processing waste streams tested including: mozzarella whey (see FIGS. 5 and 7A–7B); skim milk (see FIG. 6); swiss cheese whey (see FIG. 8); and in a composition simulating milk (see FIG. 9).

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method for enriching α(2,3) sialyllactose in a dairy source selected from the group consisting of milk, colostrum and a cheese processing mixture, comprising:

(i) contacting a catalytic amount of at least one α(2,3) trans-sialidase with the dairy source, wherein the dairy source comprises lactose and sialic acid donors to form a dairy/trans-sialidase mixture; and (ii) incubating said dairy/trans-sialidase mixture under conditions suitable to effect the α(2,3)trans-sialidase-catalyzed transfer of sialic acid from the sialic acid donors to the lactose.

2. The method of claim 1 wherein the α(2-3) trans-sialidase is a Kinetoplastid trans-sialidase.

3. The method of claim 1 wherein the α(2-3) trans-sialidase is encoded by a gene isolated from a species of the genera selected from the group consisting of Trypanosoma, Endotrypanum and Pneumocystis.

4. The method of claim 1 wherein the α(2-3) trans-sialidase is recomnbinantly produced.

5. The method of claim 1 wherein the dairy source/trans-sialidase mixture is incubated for at least 1 hour.

6. The method of claim 1 wherein the dairy source/trans-sialidase mixture is incubated at a temperature of about 5° C. to about 45° C.

7. The method of claim 1 wherein the dairy source/trans-sialidase mixture has a pH of about 6 to about 8.

8. The method of claim 1 further comprising recovering α(2-3) sialyllactose from the dairy/trans-sialidase mixture.

9. The method of claim 8 wherein the recovering step comprises ultrafiltration of the incubated dairy/trans-sialidase mixture to form an ultrafiltrate.

10. The method of claim 9 wherein the recovery step further comprises contacting said ultrafiltrate with an ion exchange resin.

11. The method of claim 10 wherein the ion exchange resin is an anion exchange resin.

12. The method of claim 10 wherein the ion exchange resin is a cation exchange resin.

13. The method of claim 8 wherein the recovering step comprises:

(a) contacting said incubated dairy source/trans-sialidase mixture of step (ii) with a solvent and extracting the α(2-3) sialyllactose with said solvent to form a α(2-3) sialyilactose containing solvent;

(b) separating said α(2-3) sialyllactose containing solvent from said incubated dairy source/trans-sialidase mixture; and (c) isolating said α(2-3) sialyllactose from said α(2-3) sialyllactose containing solvent.

14. A method for enriching α(2-3) sialyllactose in a cheese processing waste stream comprising:

(i) contacting a catalytic amount of at least one α(2-3) trans-sialidase with a cheese processing waste stream, wherein the cheese processing waste stream comprises lactose and sialic acid donors to form a waste streamltrans-sialidase mixture; and (ii) incubating said waste stream/trans-sialidase mixture under conditions suitable to effect the α(2-3) trans-sialidase-catalyzed transfer of sialic acid from the sialic acid donors to the lactose.

15. The method of claim 14 wherein said α(2-3) trans-sialidase is a Kinetoplastid trans-sialidase.

16. The method of claim 14 wherein said α(2-3) trans-sialidase is encoded by a gene isolated from a species of the genus Trypanosoma, Endotiyanum, or Pneumocystis.

17. The method of claim 14 wherein said α(2-3) trans-sialidase is recombinantly produced.

18. The method of claim 14 wherein the waste stream/trans-sialidase mixture is incubated for at least 1 hour.

19. The method of claim 14 wherein the waste stream/trans-sialidase mixture is incubated at a temperature of about 5° C. to about 45° C.

20. The method of claim 14 wherein the waste stream/trans-sialidase mixture has a pH of about 5 to about 8.

21. The method of claim 14 wherein the cheese processing waste stream comprises a member selected from the group consisting of: whole whey, demineralized whey permeate, the regeneration stream from demineralized whey permeate, whey permeate, whey powder and lactose.

22. The method of claim 14 further comprising recovering α(2-3) sialyllactose from said incubated waste stream/trans-sialidase mixture.

23. The method of claim 22 wherein the recovering step comprises ultrafiltration of the incubated waste stream/trans-sialidase mixture to form an ultrafiltrate.

24. The method of claim 23 wherein the recovering step further comprises contacting said ultrafiltrate with an ion exchange resin.

25. The method of claim 24 wherein the ion exchange resin is an anion exchange resin.

26. The method of claim 25 wherein the ion exchange resin is a cation exchange resin.

27. The method of claim 22 wherein the recovering step comprises:

(a) contacting said incubated waste stream/trans-sialidase mixture of step (ii) with a solvent and extracting said α(2-3) sialyllactose containing solvent;

(b) separating said α(2-3) sialyllactose containing solvent from said incubated waste stream/trans-sialidase mixture; and (c) isolating said α(2-3) sialyllactose from said α(2-3) sialyllactose containing solvent.

28. The method of claim 13 or 27 wherein said solvent is selected from the group consisting of water $C_1$–$C_5$ alcohol and a mixture thereof.

29. The method of claim 14 wherein said cheese processing waste stream is the mother liquor obtained by crystallizing lactose from whey.

30. The method of claim 1 or 14 wherein exogenous α(2-3) sialyloligosaccharides are added during said incubating step.

31. The method of claim 1 further comprising the step of processing the dairy/trans-sialidase mixture for cheesemaking before the recovery step.

32. The method of claim 21 wherein the lactose is crystallized lactose, spray dried lactose, or edible lactose.

33. The method of claim 1 or 14 wherein the sialic acid donors are α(2-3) sialosides.

34. The method of claim 33 wherein the α(2-3) sialosides are selected from the group consisting of κ casein, gangliosides and mixtures thereof.

35. The method of claim 1 or 14 wherein the sialic acid donors are sialyl-α(2-3)-β-galactosides.

* * * * *